United States Patent
Darby et al.

(10) Patent No.: US 12,357,488 B2
(45) Date of Patent: Jul. 15, 2025

(54) REAR ENTRY WALKER

(71) Applicant: DARCO INTERNATIONAL, INC., Huntington, WV (US)

(72) Inventors: H. Darrel Darby, Mount Pleasant, SC (US); Wu Zhang, Proctorville, OH (US)

(73) Assignee: DARCO INTERNATIONAL, INC., Huntington, WV (US)

( * ) Notice: Subject to any disclaimer, the term of this patent is extended or adjusted under 35 U.S.C. 154(b) by 0 days.

(21) Appl. No.: 17/070,569

(22) Filed: Oct. 14, 2020

(65) Prior Publication Data
US 2022/0110776 A1   Apr. 14, 2022

(51) Int. Cl.
*A61F 5/01* (2006.01)

(52) U.S. Cl.
CPC .......... *A61F 5/0195* (2013.01); *A61F 5/0111* (2013.01)

(58) Field of Classification Search
CPC .... A61F 5/0111; A61F 5/0195; A61F 5/0113; A61F 5/0127; A61F 5/0585; B29C 45/14008; B29C 45/14467
USPC .................................................... 602/23, 27
See application file for complete search history.

(56) References Cited

U.S. PATENT DOCUMENTS

| | | | |
|---|---|---|---|
| 5,078,128 A | 1/1992 | Grim et al. | |
| 5,288,286 A | 2/1994 | Davis | |
| 5,425,701 A | 6/1995 | Oster et al. | |
| 5,432,703 A * | 7/1995 | Clynch | G05B 19/4207 365/185.26 |
| 5,464,385 A | 11/1995 | Grim | |
| 5,577,998 A | 11/1996 | Johnson et al. | |
| 5,833,639 A | 11/1998 | Nunes et al. | |
| 5,891,071 A * | 4/1999 | Stearns | A61F 5/0123 602/26 |
| 6,228,044 B1 | 5/2001 | Jensen et al. | |
| 6,277,087 B1 | 8/2001 | Hess et al. | |
| 6,361,515 B1 | 3/2002 | Gilmour | |
| 6,485,447 B1 | 11/2002 | Lavery et al. | |
| 6,648,843 B1 | 11/2003 | Marciano et al. | |
| 6,682,497 B2 | 1/2004 | Jensen et al. | |
| 6,945,946 B2 | 9/2005 | Rooney | |
| 6,976,972 B2 | 12/2005 | Bradshaw | |
| 7,384,584 B2 | 6/2008 | Jerome et al. | |
| 7,418,755 B2 | 9/2008 | Bledsoe et al. | |

(Continued)

FOREIGN PATENT DOCUMENTS

| | | | |
|---|---|---|---|
| AU | 704267 B2 | 5/1997 | |
| CA | 2554869 A1 | 8/2005 | |

(Continued)

*Primary Examiner* — Ophelia A Hawthorne
*Assistant Examiner* — Michael Milo
(74) *Attorney, Agent, or Firm* — Sughrue Mion, PLLC

(57) ABSTRACT

A shell for a walker includes a base configured to receive a foot of a user thereon, a pair of side bodies extending upwards from the base, the pair of side bodies configured to cover a left side and a right side of at least one from among an ankle and a part of a lower leg of the user, respectively, while the foot of the user is received by the base, and a tibial body that is rigid and fixed to each of the pair of side bodies, the tibial body configured to cover a tibia of the user while the foot of the user is received by the base. The shell is configured to receive the foot of the user at a rear side of the shell via an opening provided between rear sides of the pair of side bodies.

18 Claims, 24 Drawing Sheets

(56) References Cited

U.S. PATENT DOCUMENTS

| | | |
|---|---|---|
| 7,727,173 B2 | 6/2010 | Rooney |
| 7,727,174 B2 | 6/2010 | Chang et al. |
| 7,758,529 B2 | 7/2010 | Jensen et al. |
| 8,002,724 B2 | 8/2011 | Hu et al. |
| 8,012,112 B2 | 9/2011 | Barberio |
| 8,021,317 B2 | 9/2011 | Arnold et al. |
| 8,226,585 B2 | 7/2012 | Pick et al. |
| 8,230,619 B2 | 7/2012 | Salvatelli et al. |
| 8,251,932 B2 | 8/2012 | Fout |
| 8,251,936 B2 | 8/2012 | Fout et al. |
| 8,454,546 B2 | 6/2013 | Campos et al. |
| 8,506,510 B2 | 8/2013 | Hu et al. |
| 9,039,645 B2 | 5/2015 | Arnold et al. |
| 9,180,038 B2 | 11/2015 | Ingimundarson et al. |
| 9,220,621 B2 | 12/2015 | Hu et al. |
| 9,333,106 B2 | 5/2016 | Hu et al. |
| 9,468,553 B2 | 10/2016 | Hu et al. |
| 9,468,555 B2 | 10/2016 | Hopmann |
| 9,492,301 B2 | 11/2016 | Hu et al. |
| 9,603,736 B1 * | 3/2017 | Buck .................. A61F 5/0195 |
| 9,668,907 B2 | 6/2017 | Romo et al. |
| 9,744,065 B2 | 8/2017 | Walborn et al. |
| 9,839,548 B2 | 12/2017 | Ingvarsson et al. |
| 9,839,549 B2 | 12/2017 | Walborn et al. |
| 9,839,550 B2 | 12/2017 | Walborn et al. |
| 10,064,749 B2 | 9/2018 | Hu et al. |
| 10,646,368 B2 | 5/2020 | Walborn et al. |
| 2002/0095105 A1 | 7/2002 | Jensen |
| 2003/0196352 A1 | 10/2003 | Bledsoe et al. |
| 2003/0212358 A1 | 11/2003 | Cavanagh et al. |
| 2005/0171461 A1 | 8/2005 | Pick |
| 2006/0178606 A1 | 8/2006 | Logue et al. |
| 2007/0038169 A1 * | 2/2007 | Alon et al. ............ A61F 5/0111 602/27 |
| 2007/0282230 A1 | 12/2007 | Valderrabano et al. |
| 2007/0293798 A1 * | 12/2007 | Hu ....................... A61F 5/0195 602/27 |
| 2009/0227927 A1 | 9/2009 | Frazer |
| 2009/0287127 A1 | 11/2009 | Hu et al. |
| 2010/0100018 A1 | 4/2010 | Fout |
| 2010/0100020 A1 | 4/2010 | Fout et al. |
| 2010/0234782 A1 | 9/2010 | Hu et al. |
| 2012/0078148 A1 | 3/2012 | Hu et al. |
| 2012/0330206 A1 * | 12/2012 | George ................. A61F 5/0111 602/27 |
| 2013/0144200 A1 | 6/2013 | Whipp |
| 2013/0310721 A1 | 11/2013 | Hu et al. |
| 2014/0197565 A1 | 7/2014 | Hu et al. |
| 2014/0257162 A1 * | 9/2014 | Falkenman ........... A61F 5/0113 29/592 |
| 2015/0088044 A1 | 3/2015 | Walborn et al. |
| 2015/0088046 A1 | 3/2015 | Walborn et al. |
| 2015/0305912 A1 | 10/2015 | Hu et al. |
| 2016/0000596 A1 | 1/2016 | Hu et al. |
| 2016/0235572 A1 | 8/2016 | Ingvarsson et al. |
| 2016/0235573 A1 | 8/2016 | Walborn et al. |
| 2016/0235578 A1 | 8/2016 | Romo et al. |
| 2017/0231796 A1 | 8/2017 | Romo et al. |
| 2017/0325984 A1 | 11/2017 | Walborn et al. |
| 2019/0240057 A1 | 8/2019 | Gunnsteinsson et al. |
| 2020/0015993 A1 * | 1/2020 | Chihlas ................. A61F 5/0111 |

FOREIGN PATENT DOCUMENTS

| | | |
|---|---|---|
| CN | 1158243 A | 9/1997 |
| CN | 102026592 B | 5/2013 |
| CN | 105899169 B | 7/2018 |
| EP | 0664110 A1 | 7/1995 |
| EP | 0770368 A1 | 5/1997 |
| EP | 1238640 A1 | 9/2002 |
| EP | 0770368 B1 | 8/2003 |
| EP | 2204146 B1 | 8/2013 |
| EP | 2862547 A1 | 4/2015 |
| EP | 2194938 B1 | 6/2015 |
| EP | 2326293 B1 | 12/2015 |
| EP | 3049035 B1 | 10/2017 |
| EP | 3034051 B1 | 8/2018 |
| EP | 3294233 B1 | 3/2019 |
| GB | 2482677 A | 2/2012 |
| WO | 94/27529 A1 | 12/1994 |
| WO | 99/11204 A1 | 3/1999 |
| WO | 00/40202 A2 | 7/2000 |
| WO | 00/40202 A3 | 7/2000 |
| WO | 03/006074 A2 | 1/2003 |
| WO | 2005/074834 A3 | 8/2005 |
| WO | 2006/110028 A1 | 10/2006 |
| WO | 2009/139893 A1 | 11/2009 |
| WO | 2011/082176 A1 | 7/2011 |
| WO | 2015/048265 A1 | 4/2015 |

* cited by examiner

300

320

318  317

400

500

700

800

900

1000

1100

1200

REAR ENTRY WALKER

FIELD

Embodiments of this disclosure are directed to a walker, specifically a rear entry walker.

BACKGROUND

Walkers, including walking boots, have been designed to limit ankle motion and to offload plantar pressure as a treatment following forefoot trauma.

SUMMARY

Comparative walker designs include stirrup walker designs and fixed/closed calf walker designs. Stirrup walker designs may include rigid side supports for an ankle and lower leg of a user, wherein a strap wraps around the side supports and the user's lower leg to secure the user's leg within the walker. That is, the stirrup walker designs do not include a fixed calf or fixed tibia portion. Fixed/closed calf walker designs may include a fixed/closed calf component and a non-fixed tibial body. For example, the tibial component of the fixed/closed calf walker designs may be simply held in place by straps to support a tibia of a user, wherein the straps wrap around the tibial component and the fixed/closed calf component.

Stirrup walker designs may still allow for unintended movement of an ankle joint of a user, thereby causing increases forefoot pressure that reduces effectiveness of treatment. Fixed/closed calf walker designs may only accommodate calves of certain sizes due to the fixed size of the fixed/closed calf component. Moreover, fixed/closed calf walker designs may also allow for unintended movement of an ankle joint of a user due to the unfixed nature of the tibial component.

Some embodiments of the present disclosure address the above problems and other problems of comparative designs.

For example, some embodiments of the present disclosure provide walkers and walker shells that may be more lightweight and have stronger structures, while enabling a reduction in plantar pressure by limiting ankle joint movement and providing pressure offloading. Moreover, some embodiments of the present disclosure provide walkers and walker shells that are capable of being applied to users having a large range of calf sizes. Thus, embodiments of the present disclosure may provide an advantageous treatment option in cases related to, for example, forefoot surgery, forefoot trauma, and diabetes-related foot issues.

According to one or more embodiments, a shell for a walker is provided. The shell includes a base configured to receive a foot of a user thereon; a pair of side bodies extending upwards from the base, the pair of side bodies configured to cover a left side and a right side of at least one from among an ankle and a part of a lower leg of the user, respectively, while the foot of the user is received by the base; and a tibial body that is rigid and fixed to each of the pair of side bodies, the tibial body configured to cover a tibia of the user while the foot of the user is received by the base.

According to an embodiment, the tibial body is integrally formed with each of the pair of side bodies.

According to an embodiment, the pair of side bodies are integrally formed with the base.

According to an embodiment, the shell is configured to receive the foot of the user at a rear side of the shell via an opening provided between rear sides of the pair of side bodies.

According to an embodiment, the pair of side bodies or the tibial body is configured to connect to a strap that extends across a calf of the user by extending across the opening.

According to an embodiment, at least one from among the tibial body and the pair of side bodies is configured to connect to a tibial liner.

According to an embodiment, at least a portion of the tibial body is rigidly fixed to each of the pair of side bodies.

According to an embodiment, at least one from among the base and the pair of side bodies is configured to connect to a strap that extends across a top side of the foot of the user or a front side of an ankle of the user.

According to one or more embodiments, a walker is provided. The walker includes a liner configured to surround a portion of a foot of a user and a part of a lower leg of the user; and a shell including: a base configured to receive the foot of the user, within the liner, thereon; a pair of side bodies extending upwards from the base, the pair of side bodies configured to cover a left side and a right side of at least one from among an ankle and the part of the lower leg of the user, respectively, while the foot of the user is received by the base; and a tibial body that is rigid and fixed to each of the pair of side bodies, the tibial body configured to cover a tibia of the user while the foot of the user is received by the base.

According to an embodiment, the tibial body is integrally formed with each of the pair of side bodies.

According to an embodiment, the pair of side bodies are integrally formed with the base.

According to an embodiment, the shell is configured to receive the foot of the user at a rear side of the shell via an opening provided between rear sides of the pair of side bodies.

According to an embodiment, the walker further includes a strap, wherein the pair of side bodies or the tibial body is configured to connect to the strap such that the strap extends across a calf of the user by extending across the opening.

According to an embodiment, the walker further includes a tibial liner, wherein at least one from among the tibial body and the pair of side bodies is configured to connect to the tibial liner.

According to an embodiment, at least a portion of the tibial body is rigidly fixed to each of the pair of side bodies.

According to an embodiment, the walker further includes a strap, wherein at least one from among the base and the pair of side bodies is configured to connect to the strap such that the strap extends across a top side of the foot of the user or a front side of an ankle of the user.

According to one or more embodiments, a rear-entry walker is provided. The rear-entry walker includes a shell including: a base configured to receive a foot of a user thereon; a pair of side bodies extending upwards from the base, the pair of side bodies configured to cover a left side and a right side of at least one from among an ankle and a part of a lower leg of the user, respectively, while the foot of the user is received by the base; and a tibial body that is rigid and fixed to each of the pair of side bodies, the tibial body configured to cover a tibia of the user while the foot of the user is received by the base, wherein the shell is configured to receive the foot of the user at a rear side of the shell via an opening provided between rear sides of the pair of side bodies.

According to an embodiment, the rear-entry walker further includes a tibial liner provided on an inner surface of the tibial body.

According to an embodiment, at least one from among the tibial body and the pair of side bodies is connected to the tibial liner.

According to an embodiment, at least a portion of the tibial body is rigidly fixed to each of the pair of side bodies.

BRIEF DESCRIPTION OF THE DRAWINGS

Further features, the nature, and various advantages of the disclosed subject matter will be more apparent from the following detailed description and the accompanying drawings in which.

DETAILED DESCRIPTION

Figure 1:
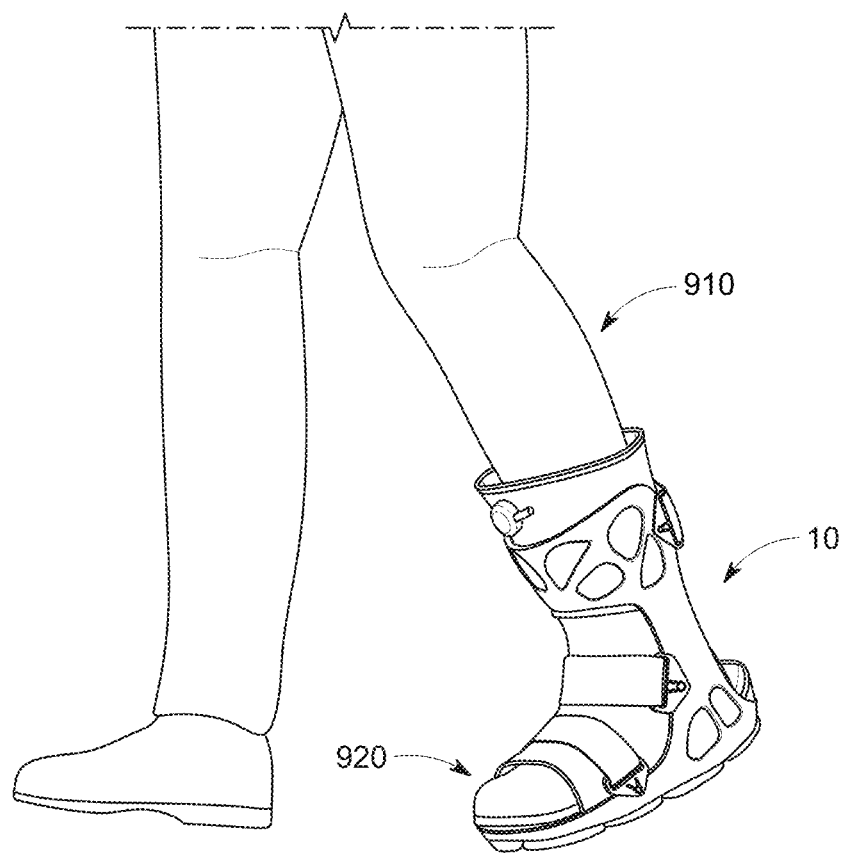
FIG. 1 illustrates a walker of an embodiment of the present disclosure on a user.
Figure 2:
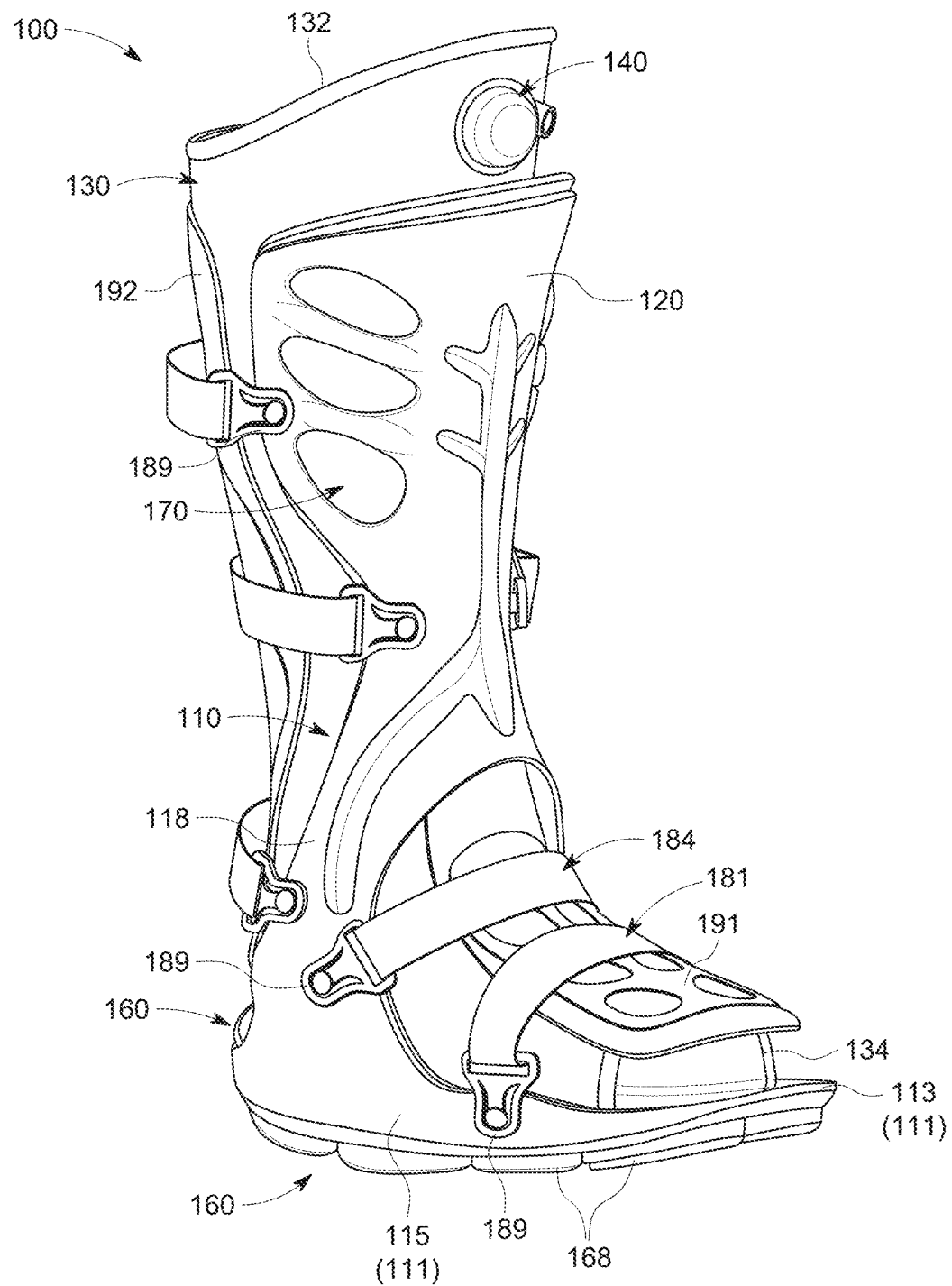
FIG. 2 illustrates a perspective view of a walker of an embodiment of the present disclosure.

According to an embodiment of the present disclosure, with reference to FIG. 1, a walker 10 may be provided. The walker 10 may be applied to a foot 920 and a lower leg 910 of a user. The walker 10 may correspond to walkers of the present disclosure. For example, the walker 10 may correspond to the walker 100 described below.

With reference to FIGS. 2-12, the walker 100 may comprise a shell 110, a liner 130, an air pump 140, a footbed liner 150, an outsole 160, a tibial liner 170, a first strap 181, a second strap 184, and a third strap(s) 187.

Figure 9:
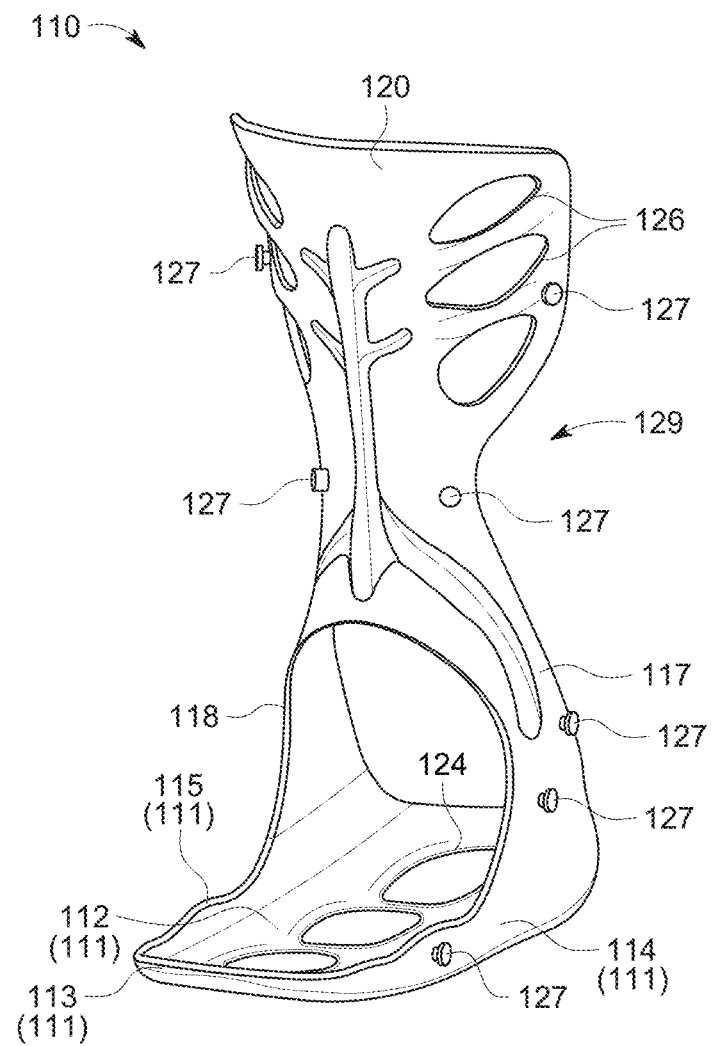
FIG. 9 illustrates a perspective view of a shell of the walker of the embodiment of the present disclosure.
Figure 10:
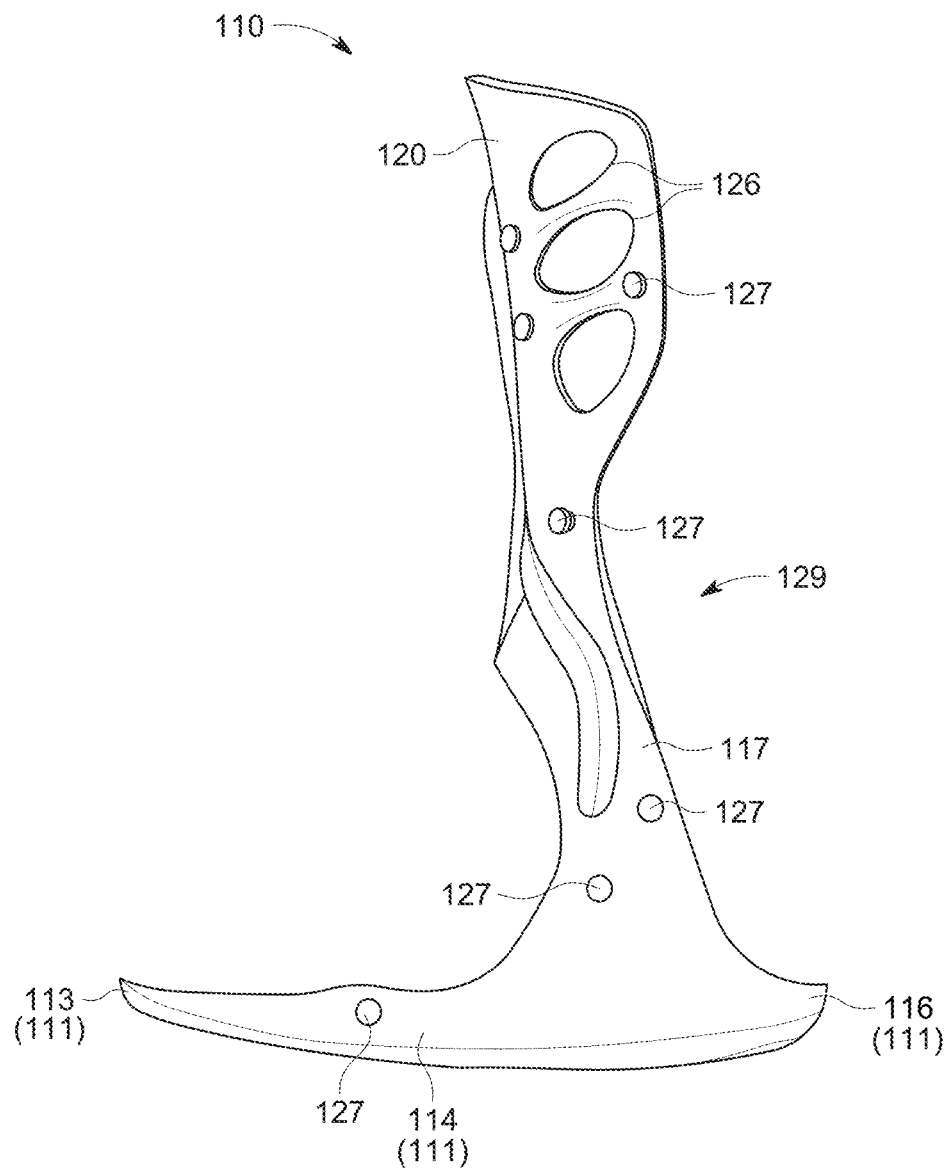
FIG. 10 illustrates a side view of the shell of the walker of the embodiment of the present disclosure illustrated in FIG. 9.
Figure 11:
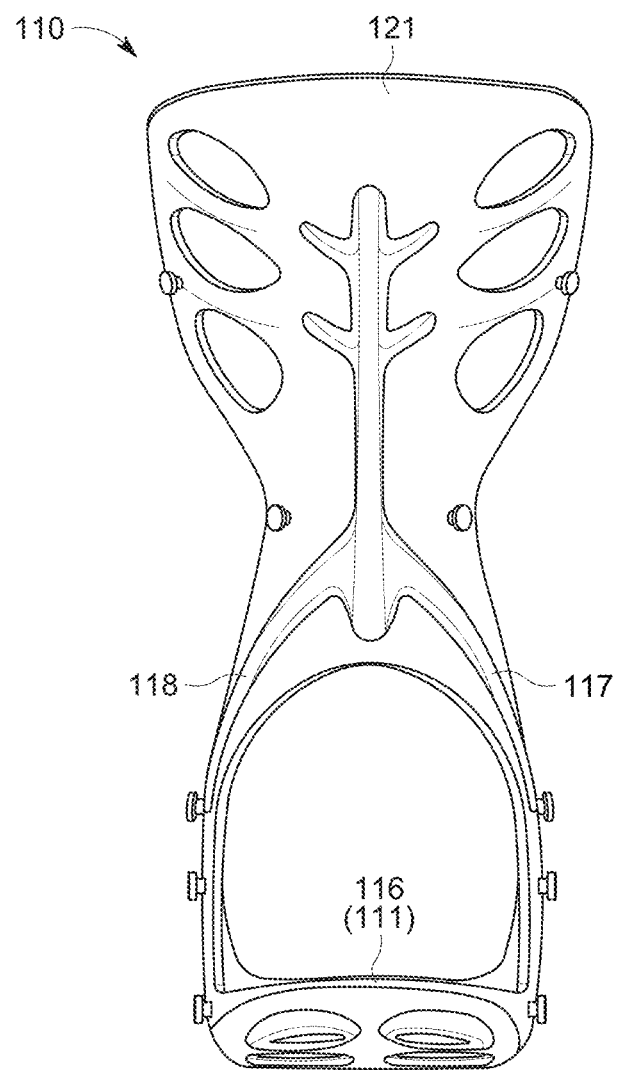
FIG. 11 illustrates a front view of the shell of the walker of the embodiment of the present disclosure illustrated in FIG. 9.

The shell 110 of the walker 100 may be configured to limit motion of the foot 920, ankle, and leg of the user, and provide additional offloading to the forefoot of the user. With reference to FIG. 9, the shell 110 of the walker 100 may comprise a shell base 111, a left side body 117, a right side body 118, and a tibial body 120. The shell base 111 may be configured to receive the foot 920 of the user, and the shell base 111 may comprise a bottom plate 112, a front wall 113, a left wall 114, a right wall 115, and a rear wall 116. The shell base 111 may be configured to receive the foot 920 of the user thereon. The left wall 114 of the shell base 111 may be connected to the left side body 117, and the right wall 115 of the shell base 111 may be connected to the right side body 118.

The left side body 117 and the right side body 118 may each be in a plate shape and extend upwards from the left wall 114 and the right wall 115, respectively, so as to be configured to support left and right sides of at least one from among an ankle and a portion of the lower leg 910 of the user, respectively. The left side body 117 and the right side body 118 may be rigid.

Figure 12:
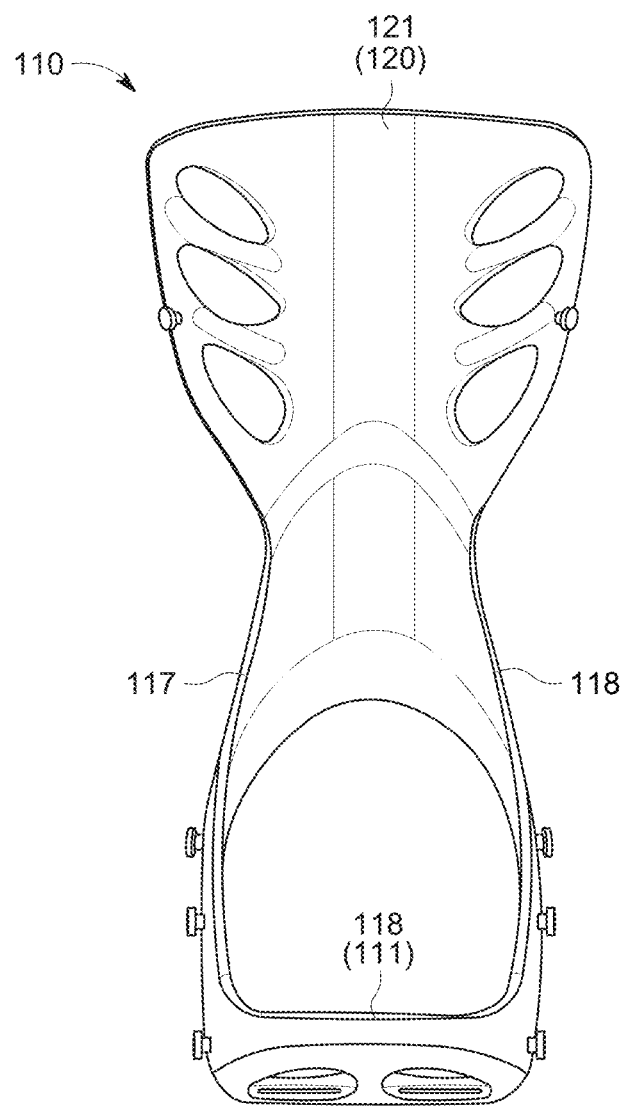
FIG. 12 illustrates a rear view of the shell of the walker of the embodiment of the present disclosure illustrated in FIG. 9.

At a front side (the tibial side) of the left side body 117 and the right side body 118, a tibial body 120 may be provided between the left side body 117 and the right side body 118. The tibial body 120 may be configured to support the tibia of the user. The tibial body 120 may be connected to the left side body 117 and the right side body 118 so as to be rigidly fixed therebetween. A portion of the tibial body 120 may be considered to be "rigidly fixed" when the tibial body 120 is secured to the left side body 117 and the right side body 118 such that the portion of the tibial body 120 is prohibited from translationally moving relative to the left side body 117 and the right side body 118, in at least one direction (e.g. a front-back direction), even when the foot 920 is not in the walker 100. For example, a tibial body may be "rigidly fixed" when integrally provided with the side bodies or via removable or non-removable attachment to side bodies as illustrated in, for example, FIGS. 9, 16-20, and 22-25. Accordingly, a cord system or non-rigid straps may not be needed to hold the tibial body 120 at least partially in place. As illustrated in FIG. 9, the tibial body 120 may be integrally formed with the left side body 117 and the right side body 118. Alternatively, the tibial body 120 may be rigidly fixed to the left side body 117 and the right side body 118 via fasteners such as, for example, screws, bolts, pins, clips, rivets, etc. The tibial body 120 may be in a plate shape and may be rigid. As illustrated in FIG. 12, the tibial body 120 may have a curved shape so to circumferentially surround the tibia of a user.

At a rear side (calf side) of the left side body 117 and the right side body 118, an opening 129 may be provided. The shell 110 may be configured to receive the foot 920 of the user via the opening 129. Accordingly, the walker 100 may be configured as a rear-entry walker. Due to the opening 129 enabling a calf of a user to be exposed from the shell 110, the shell 110 may accommodate calves of varying sizes.

The shell 110 may further include attachment portions that enable attachment of other components of the walker 100 to the shell 110. For example, the bottom plate 112 of the shell base 111 may include holes 124 for attaching the outsole 160, and the left wall 114 and the right wall 115 of the shell base 111. Alternatively or additionally, according to embodiments, the left side body 117 and the right side body 118 may include one or more holes for attaching the footbed liner 150, and the left side body 117 and the right side body 118. Alternatively or additionally, the tibial body 120 may include one or more holes 126 for attaching the tibial liner 170. Alternatively or additionally, the shell 110 may include protrusions 127 for attaching one or more straps, such as a first strap 181, second strap 184, and third strap(s) 187. The straps may be, for example, Velcro straps.

With reference to FIGS. 2-12, the outsole 160 may be configured to provide traction, shock absorption, and off-loading while walking. The outsole 160 may comprise a base 162 and one or more protrusions 168 that project from a bottom surface of the base 162. When assembled in the walker 100, the bottom surface of the base 162 may be provided to contact a top surface of the bottom plate 112 of the shell base 111. That is, the base 162 may be provided in an interior of the shell base 111, between the front wall 113, the left wall 114, the right wall 115, and the rear wall 116 of the shell base 111. The protrusions 168 of the outsole 160 may be configured to be fitted through the holes 124 of the bottom plate 112 of the shell base 111 such that the protrusions 168 extend below the bottom surface of the bottom plate 112 of the shell base 111. Accordingly, the outsole 160 may be connected to the shell 110, and the protrusions 168 may be configured as an outermost layer of a sole of the walker 100. In an embodiment, the protrusions 168 may be configured to snap-fit to the holes 124.

The footbed liner 150 may be configured to provide padding across the sole of the foot 920 of the user. The footbed liner 150 may comprise a bottom part 152, side walls 153, and a rear wall 154. When assembled in the walker 100, a bottom surface of the bottom part 152 may be provided to contact the top surface of the base 162 of the outsole 160. A top surface of the bottom part 152 may be configured to receive the foot 920 of the user thereon. One of the side walls 153 of the footbed liner 150 may be configured to cover an inner side of the left wall 114 of the shell 110 and/or an inner side of the left side body 117 of the shell 110. Another of the side walls 153 of the footbed liner 150 may be configured to cover an inner side of the right wall 115 of the shell 110 and/or an inner side of the right side body 118 of the shell 110.

According to an embodiment, an outer side of each of the side walls 153 of the footbed liner 150 may include one or more of protrusions. The protrusions may be configured to extend into respective ones of holes of the shell 110. Accordingly, the footbed liner 150 may be connected to the shell 110, and the outsole 160 may be further secured between the shell 110 and the footbed liner 150. In an embodiment, the protrusions may be configured to snap-fit to the holes.

The tibial liner 170 may be configured to provide additional padding between where the tibia of the user meets the shell 110 (e.g. the tibial body 120). The tibial liner 170 may comprise a body 172. The body 172 of the tibial liner 170 may be configured to line an inner surface 121 of the tibial body 120, and may provide cushion to the tibial of the user of the walker 100. In an embodiment, the body 172 of the tibial liner may be attached to the left side body 117 and the right side body 118 of the shell 110 and/or the tibial body 120 of the shell 110. According to an embodiment, protrusions may project from an outer surface of the body 172 of the tibial liner, and the protrusions may be configured to extend into respective ones of the holes 126, on an inner side of the shell 110, toward an outer side of the shell 110. Accordingly, the tibial liner 170 may be connected to the shell 110. In an embodiment, the protrusions of the tibial liner 170 may be configured to snap-fit to the holes 126.

The liner 130 may be padded cushion configured to provide compression and padding to the lower leg 910 of the user. The liner 130 may be configured to receive and surround the foot 920 and a portion of the lower leg 910 of the user. For example, the foot 920 and the portion of the lower leg 910 may be inserted into a first opening 132 of the liner 130. In an embodiment, a front portion (e.g. toes) of the foot 920 of the user may protrude out of a second opening 134 of the liner 130 when the foot 920 is within the liner 130. When provided in the walker 100, a bottom portion of the liner 130 may directly contact, for example, the top surface of the bottom part 152 of the footbed liner 150, inner surfaces of the side walls 153 and rear wall 154 of the footbed liner 150, and an inner surface 121 of the tibial body 120 of the shell 110. In an embodiment, the liner 130 may be provided with an air pump 140 that is configured to change an air pressure of the liner 130. For example, the air pump 140 may be configured to cause inflation and deflation of an air bag of the liner 130 to control compression levels.

The foot 920 and the portion of the lower leg 910 of the user, within the liner 130, may be secured within the walker 100 by one or more straps (e.g., first strap 181, second strap 184, and/or third strap(s) 187).

Figure 3:
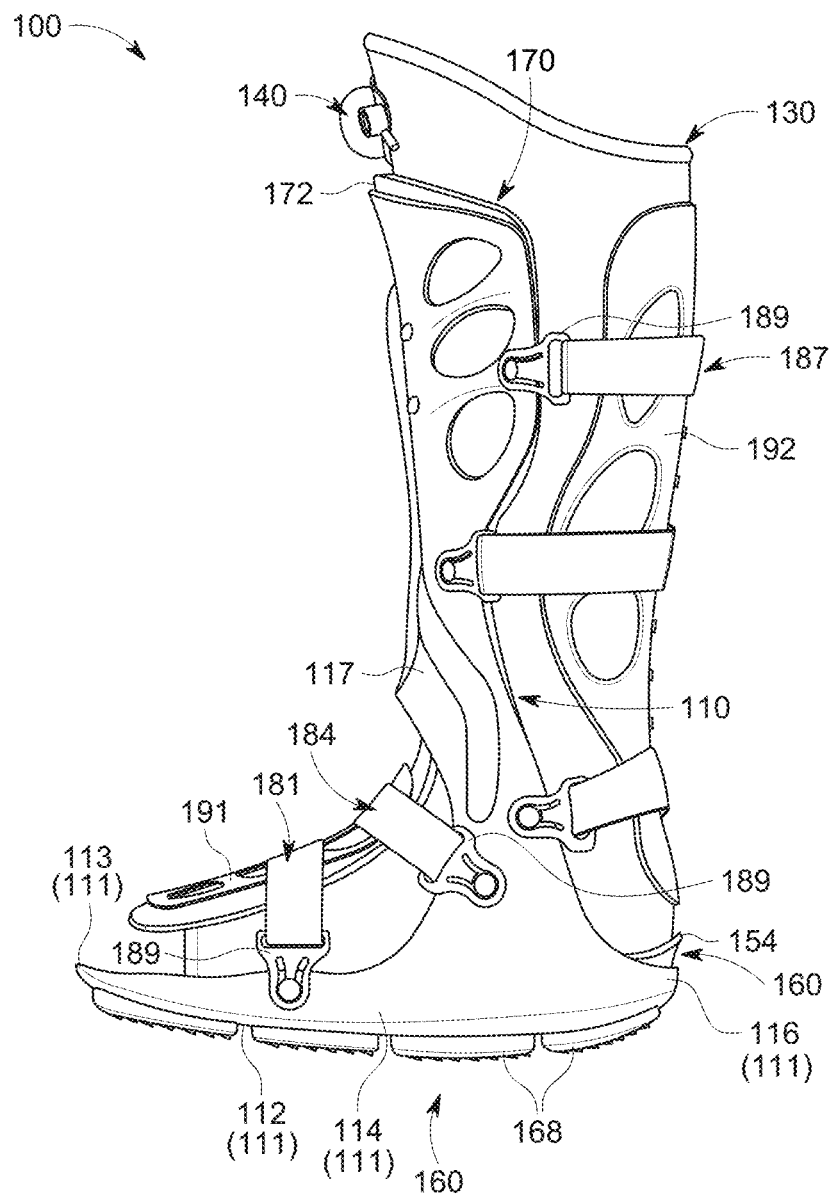
FIG. 3 illustrates a side view of the walker of the embodiment of the present disclosure illustrated in FIG. 2.
Figure 4:
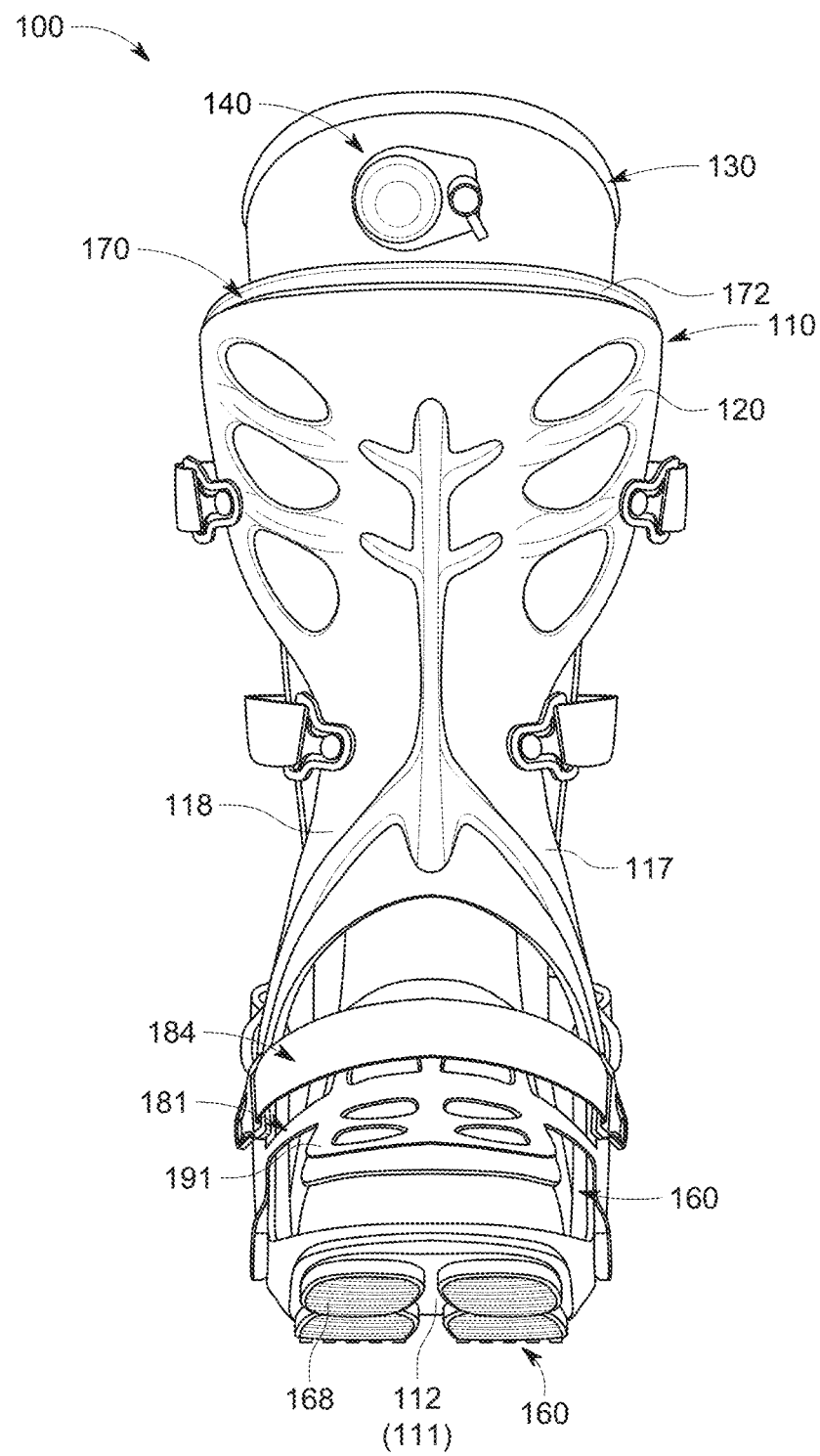
FIG. 4 illustrates a front view of the walker of the embodiment of the present disclosure illustrated in FIG. 2.

For example, the first strap 181 may be configured to cover and secure a front part (e.g. toes) of the foot 920 of the user that is within the liner 130, the second strap 184 may be configured to cover and secure a front of an ankle of the user that is within the liner 130. According to embodiments, the walker 100 may include a front body 191 that is configured to cover a top of the foot 920, and the first strap 181 and the second strap 184 may be configured to hold the front body 191 in place on a portion of the tibial liner 170. For example, the portion of the tibial liner 170 may extend to the front part (e.g. toes) of the foot 920 as illustrated in FIG. 3. According to embodiments, the front body 191 may be rigid.

Figure 5:
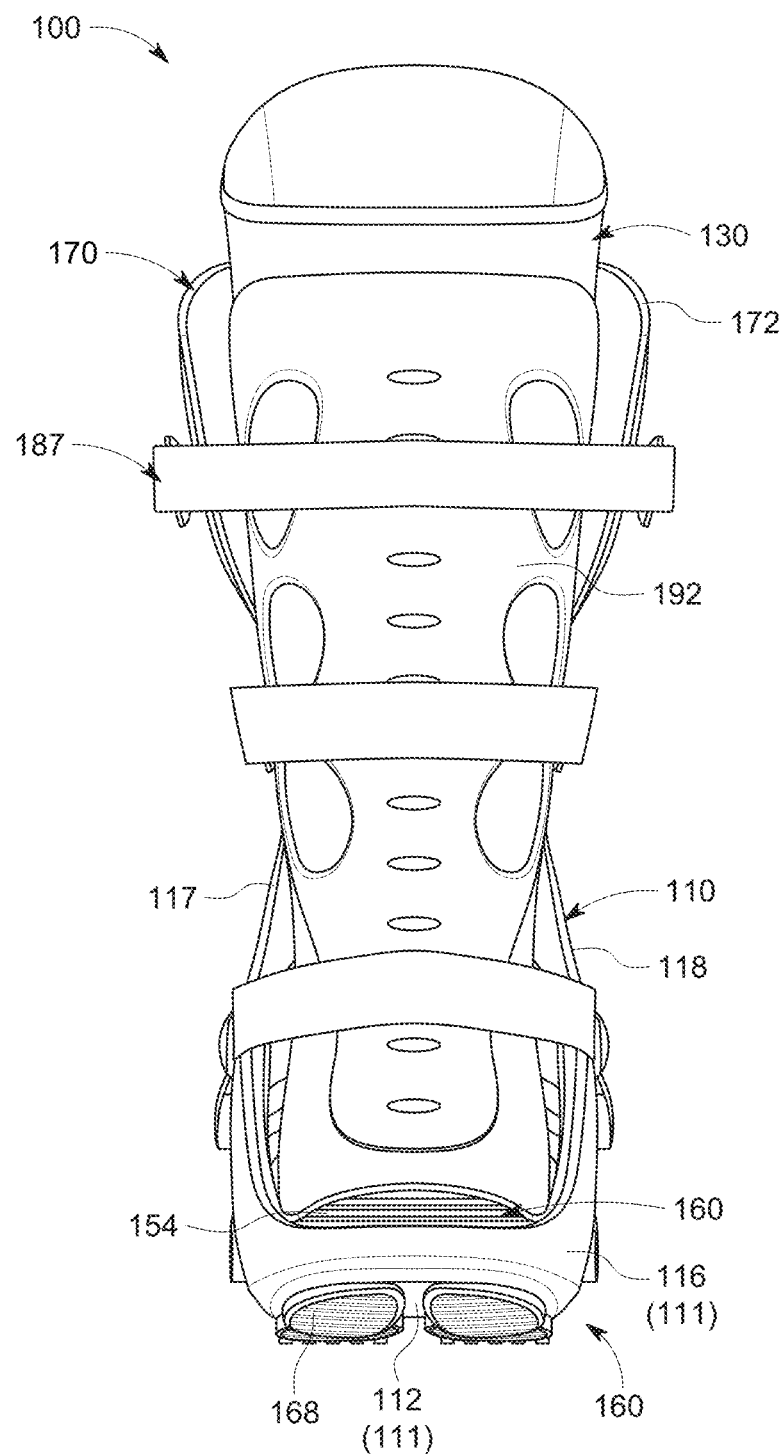
FIG. 5 illustrates a rear view of the walker of the embodiment of the present disclosure illustrated in FIG. 2.
Figure 6:
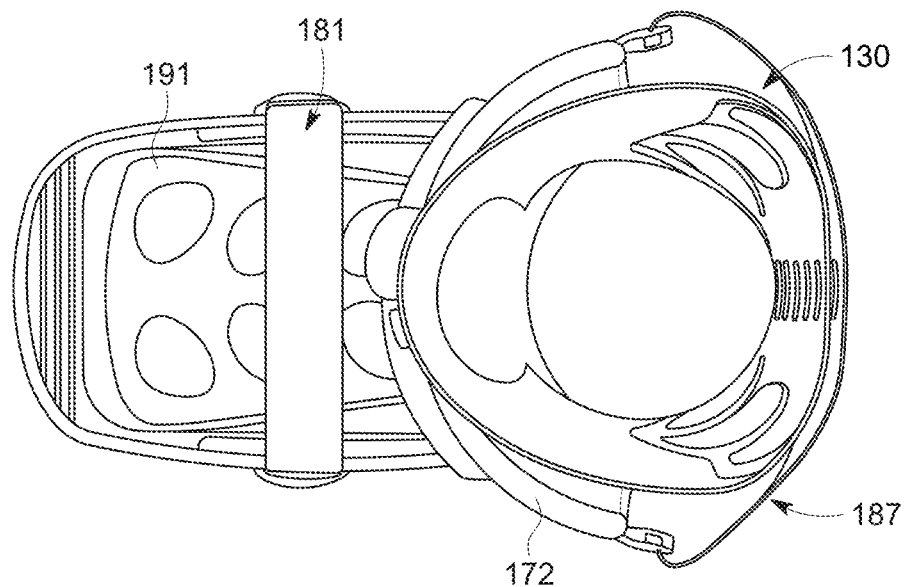
FIG. 6 illustrates a top view of the walker of the embodiment of the present disclosure illustrated in FIG. 2.
Figure 7:
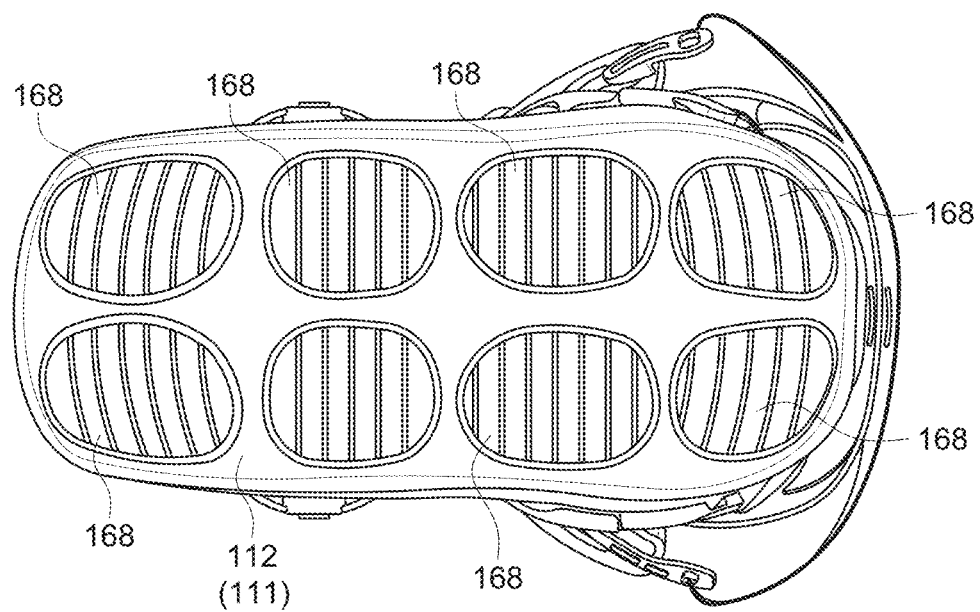
FIG. 7 illustrates a bottom view of the walker of the embodiment of the present disclosure illustrated in FIG. 2.
Figure 8:
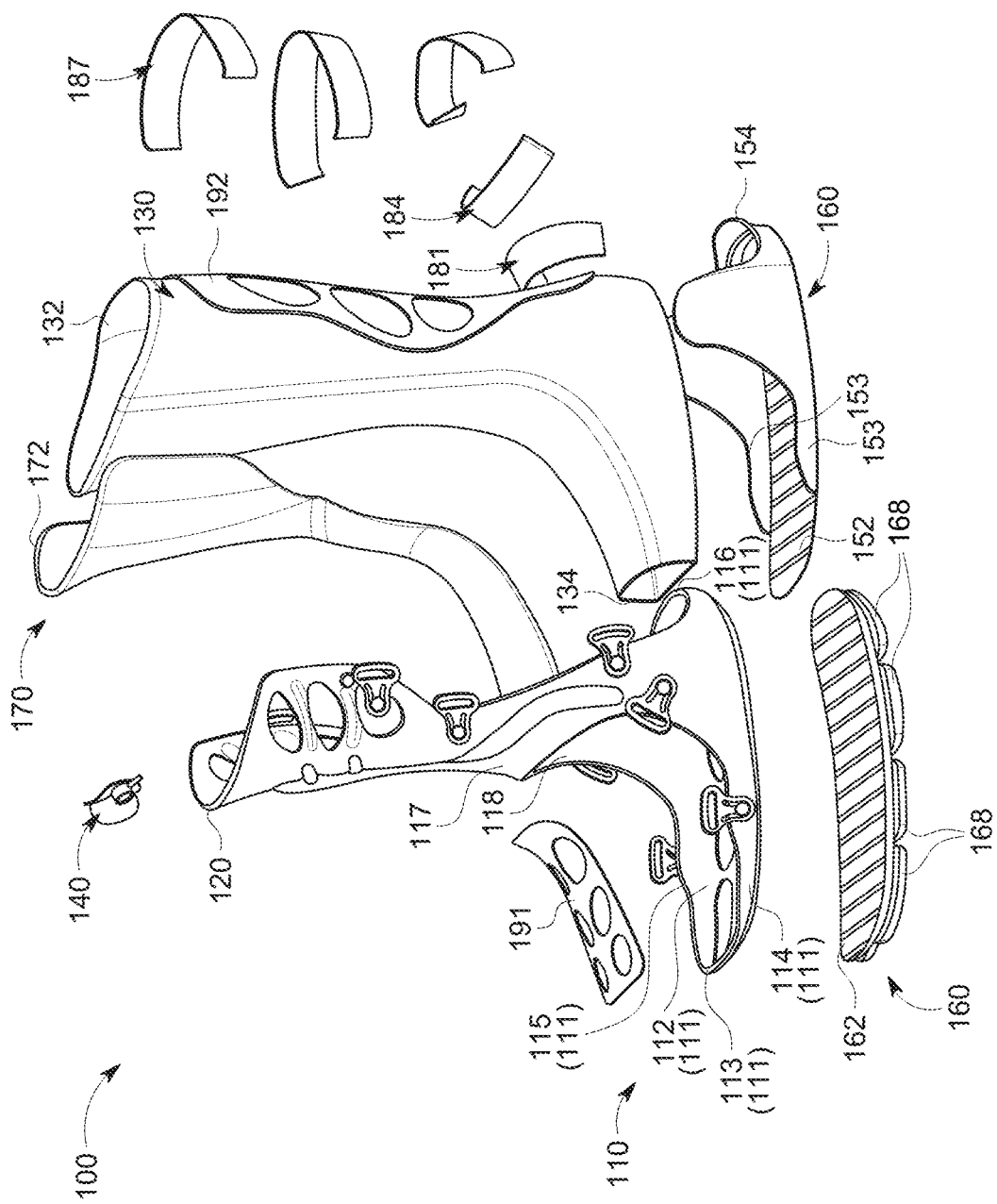
FIG. 8 illustrates an exploded view of the walker of the embodiment of the present disclosure illustrated in FIG. 2.

The third strap(s) 187 may be configured to cover and secure a back of the leg (e.g. the calf) of the user that is within the liner 130. According to embodiments, as illustrated in FIGS. 5 and 8, the walker 100 may include a rear body 192 that is configured to cover the back side of the lower leg 910 of the user, and the third strap(s) 187 may be configured to hold the rear body 192 in place on the liner 130. According to embodiments, the rear body 192 may be rigid.

Each of the first strap 181, the second strap 184, and the third strap(s) 187 may be provided with a respective connector 189 on both ends thereof, wherein each connector 189 is configured to connect to a respective one of the protrusions 127 of the shell 110. In an embodiment, each connector 189 may include at least one hole that is configured to snap-fit to one of the protrusions 127. In an embodiment, the outer sides of the shell 110 are where the protrusions 127 are provided. According to embodiments, the shell 110 may include holes instead of the protrusions 127, and each connector 189 may include a protrusion that is configured to snap fit into ones of the holes of the shell 110.

Figure 13:
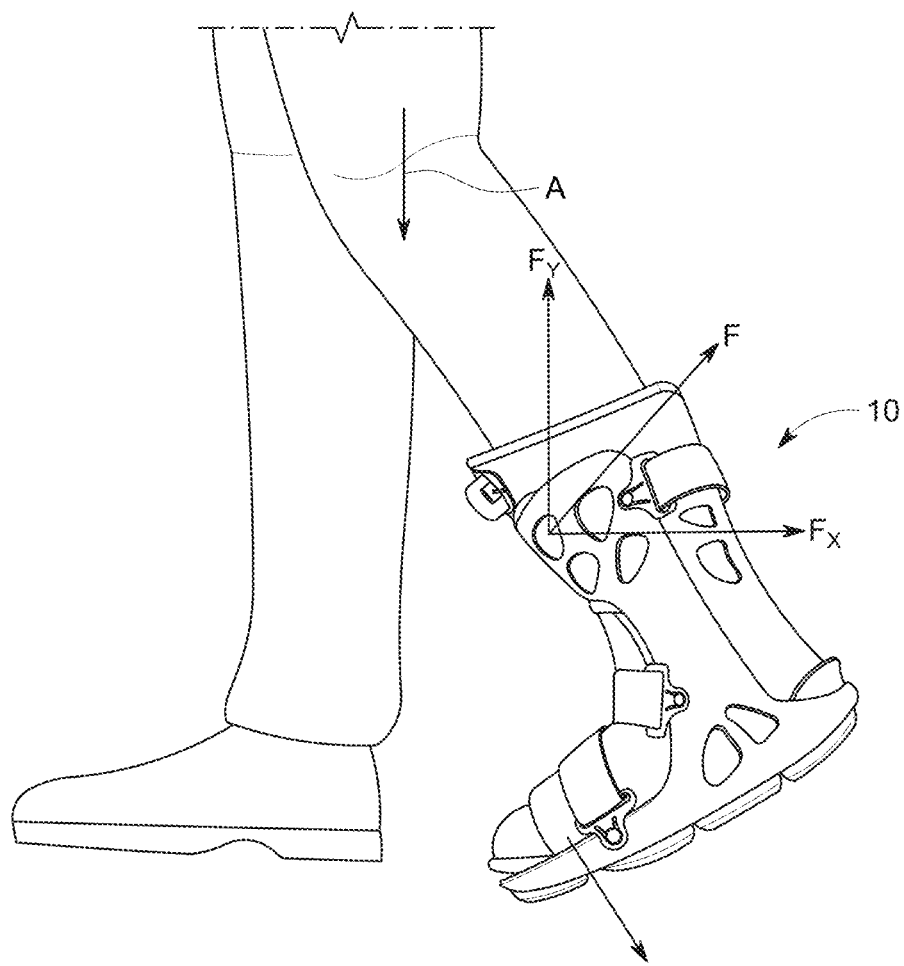
FIG. 13 is a first diagram illustrating forces applied when a walker of an embodiment of the present disclosure is worn by the user.
Figure 14:
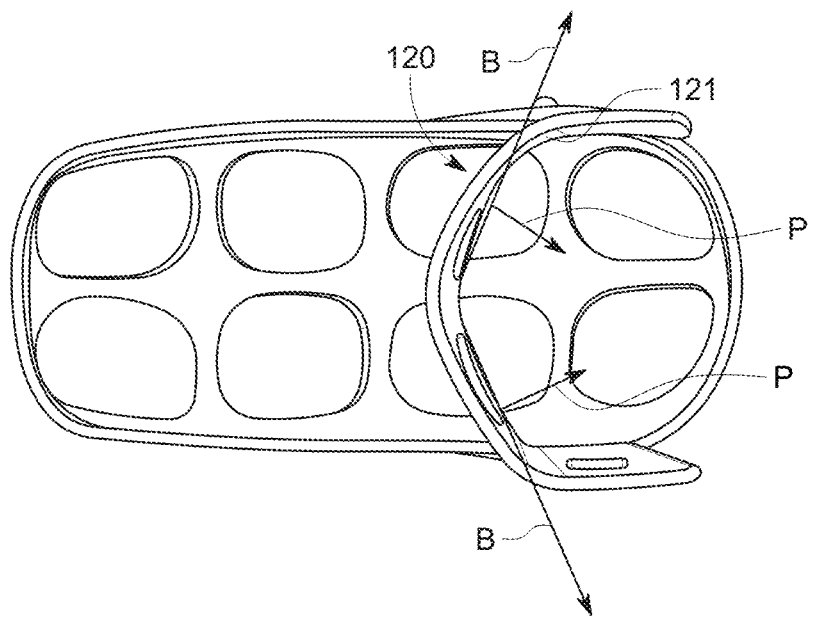
FIG. 14 is a second diagram illustrating forces applied when the walker of the embodiment of the present disclosure is worn by the user.
Figure 15:
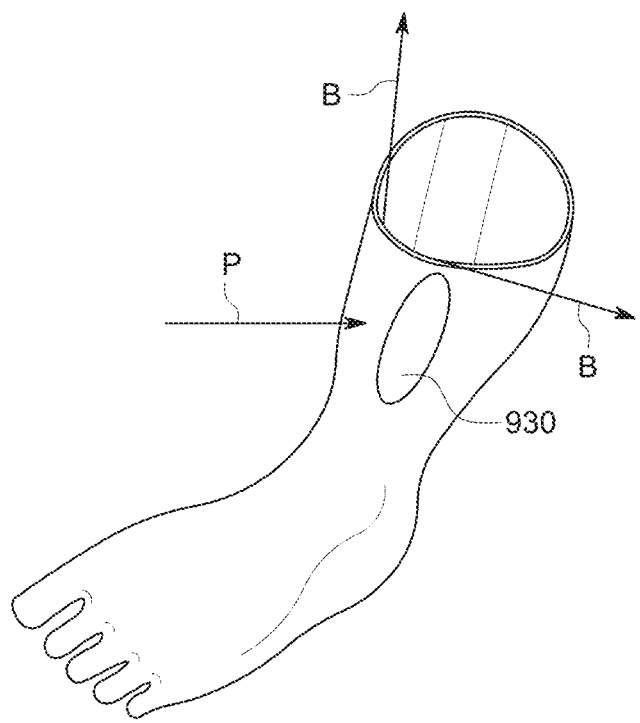
FIG. 15 is a third diagram illustrating forces applied when the walker of the embodiment of the present disclosure is worn by the user.

With reference to FIG. 13, a user generates a downward force A when they walk, which produces a forefoot pressure. The forefoot pressure is increased in a case where ankle joint movement is increased. In an embodiment of the present disclosure, the tibial body 120 of the walker 10 reduces ankle joint movement and enables offloading of pressure with force F (including components Fx and Fy) to be distributed to the shin of the user instead of as forefoot pressure. For example, with reference to FIGS. 14-15, the inner surface 121 of the tibial body 120 may transfer pressure P to zones of the lower leg 910 of the user, including a zone 930. As illustrated in FIG. 14, the inner surface 121 of the tibial body 120 may have a subtle triangular shape (or bend) when viewed in a top view. With reference to the imaginary lines B that extend away from a center of the inner surface 121, such a shape may prevent the tibial body 120 from coming in direct contact with a tibia bone of a leg. Instead, with reference to FIG. 15, muscles on the sides of the leg may rest on the inner surface 121 of the tibial body to absorb the applied forces such that no forces are directly applied to the tibia bone. For example, the pressure P may be applied to the zone 930, that corresponds to the gastrocnemius muscle, and the pressure P may also be applied to another zone on the inner side of the leg, that corresponds to the tibialis anterior muscle. According to the above, plantar pressure may be reduced by offloading and tibia discomfort may be avoided. In comparison with comparative stirrup walker designs, embodiments of the present disclosure have been measured to provide a 22%-24% decrease in plantar pressure.

Figure 16:
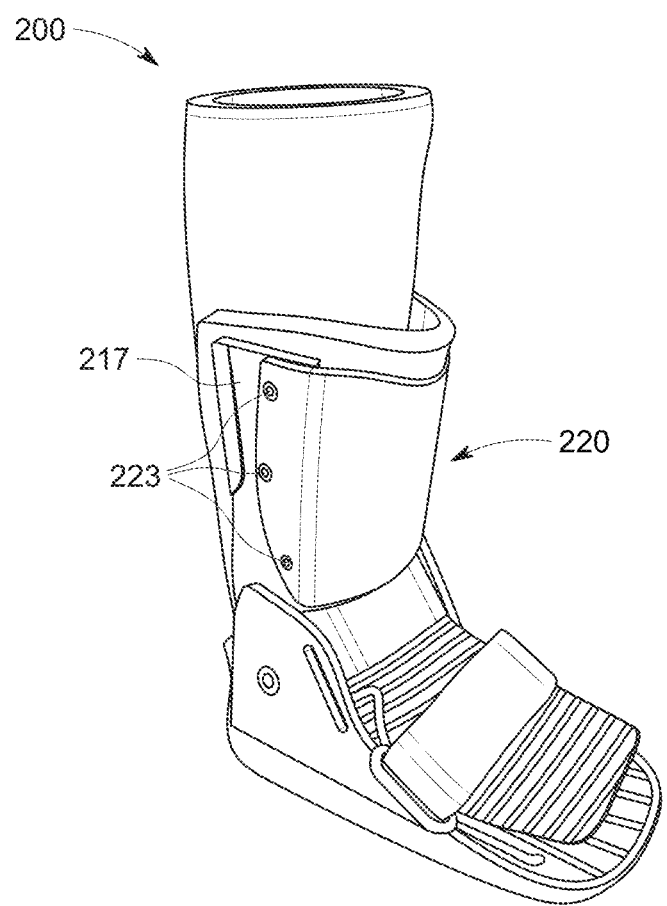
FIG. 16 illustrates a perspective view of a walker of an embodiment of the present disclosure.

As another example of an embodiment of the present disclosure, FIG. 16 illustrates a walker 200. The walker 200 may be the same as walker 100, except for some differences. For example, the walker 200 may comprise a tibial body 220 instead of a tibial body 120. The tibial body 220 may be fixed to side bodies 217 (corresponding to the left side body 117 and the right side body 118) via fasteners 223. The fasteners 223 may be any kind of fastener including, for example, screws, bolts, pins, clips, rivets, etc.

According to embodiments, any number of the components of the walker 100 and the walker 200 may be made of, for example, nylon, polypropylene, polycarbonate (PC), acrylonitrile butadiene styrene (ABS), aluminum, and/or steel. For example, the shell 110, including the shell base 111, the left side body 117, the right side body 118, and the tibial body 120 may be made of such material(s).

Further example embodiments of the present disclosure are described below with reference to FIGS. 17-26. The example embodiments described below may incorporate any number of the aspects of the walker 100 and the walker 200.

According to embodiments, a walker with a fully-removable tibial plate with a fixed angle may be provided. For example, a tibial plate (e.g. tibial body), stirrups (e.g. left side body and right side body), and a footbed (e.g. shell base) of a walker shell may not all be integrally molded together, and the walker may be configured such that an angle of the tibial plate cannot be altered so as to improve patient comfort or shifting offloading.

Figure 17:
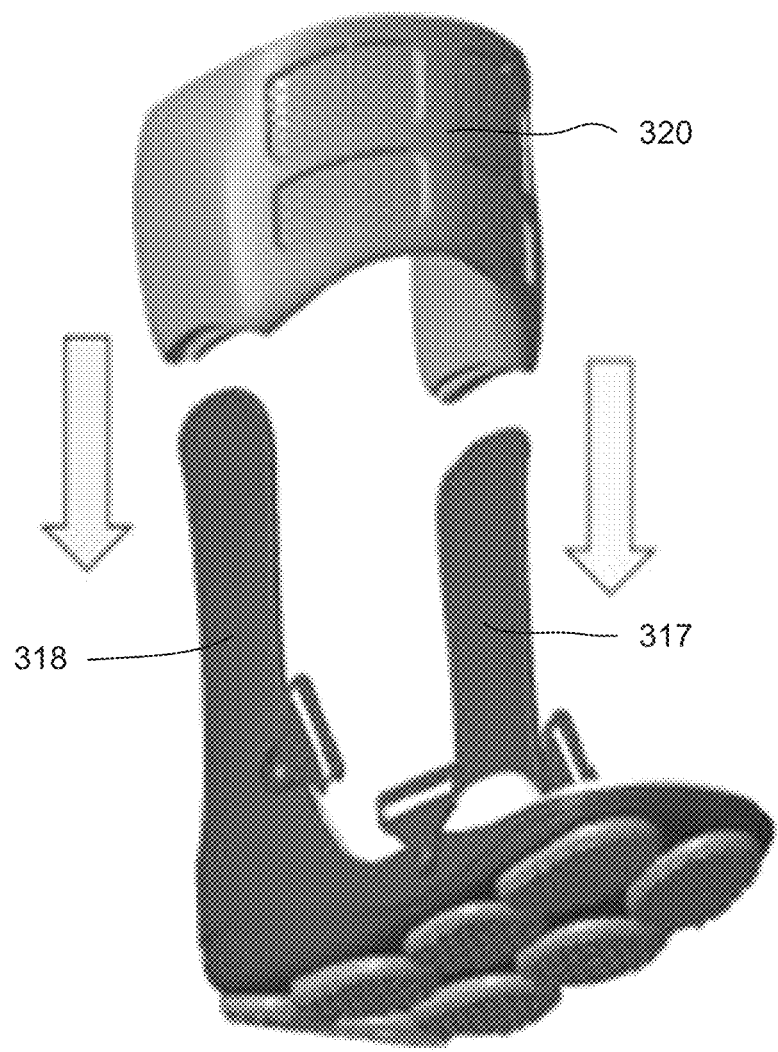
FIG. 17 illustrates a perspective, exploded view of a walker of an embodiment of the present disclosure.

In one example embodiment, referring to FIG. 17, a stirrup walker 300 may be retrofitted with a tibial body 320 (e.g. a tibial plate) that is configured to slip over stirrups (e.g. the left side body 317 and the right side body 318). According to an embodiment, the tibial body 320 may include interior spaces that are configured to receive the stirrups. By the stirrups being inserted into the tibial body 320, the tibial body 320 may be rigidly fixed to the stirrups.

Figure 18:
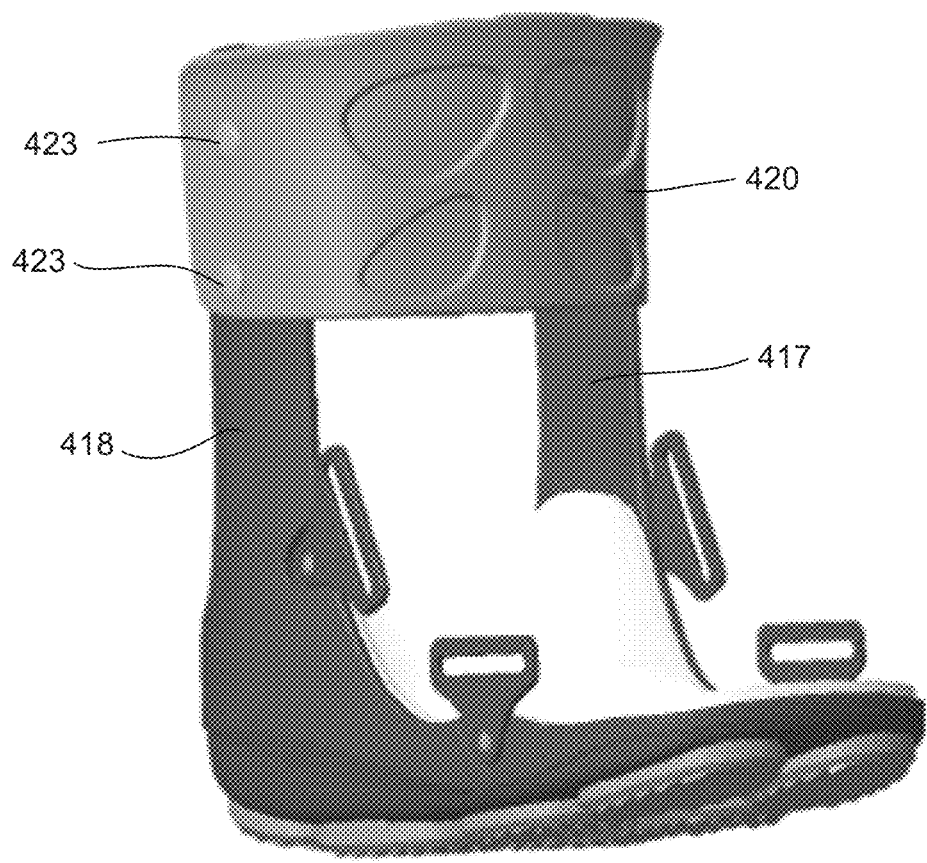
FIG. 18 illustrates a perspective view of a walker of an embodiment of the present disclosure.

In another example embodiment, referring to FIG. 18, a walker 400 may include fasteners 423 that are configured to fix a tibial body 420 (e.g. a tibial plate) to the left side body 417 and the right side body 418. The fasteners 423 may be, for example, rivets, nuts, and bolts, etc., that may or may not be removable. In such configuration, the tibial body 420 may be rigidly fixed to the left side body 417 and the right side body 418.

Figure 19:
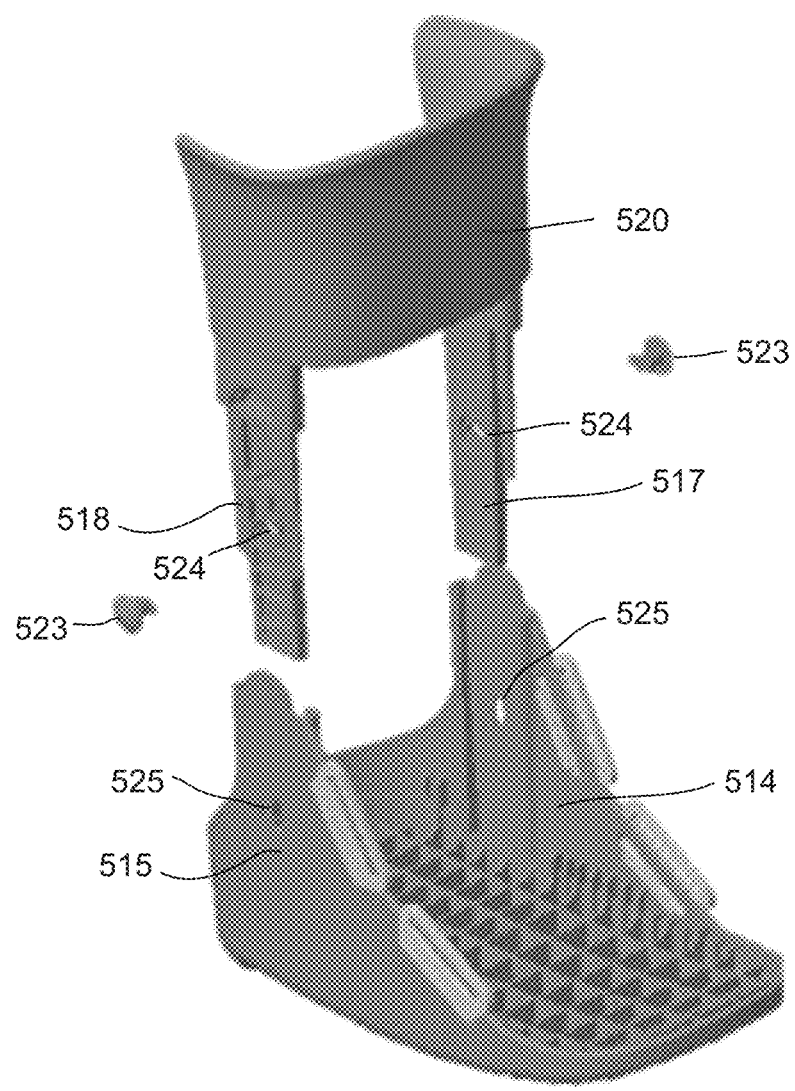
FIG. 19 illustrates a perspective, exploded view of a walker of an embodiment of the present disclosure.

In another example embodiment, referring to FIG. 19, a walker 500 may include a tibial body 520 (e.g. a tibial plate) that is integrally molded with stirrups (e.g. a left side body 517 and a right side body 518). The stirrups may be configured to attach to a separate footbed component (e.g. a shell base that includes a left side wall 514 and a right side wall 515). For example, fasteners 523 (e.g. projecting bodies) may be provided that are configured to be inserted through holes 525 of the left side wall 514 and the right side wall 515 and through holes 524 of the left side body 517 and the right side body 518, while the holes 525 and the holes 524 are aligned, such that the stirrups (with the tibial body 520) and the shell base are fixed together. In such configuration, the tibial body 520 may be rigidly fixed to the left side body 517 and the right side body 518, and the left side body 517 and the right side body 518 may be rigidly fixed to the shell base.

Figure 20:
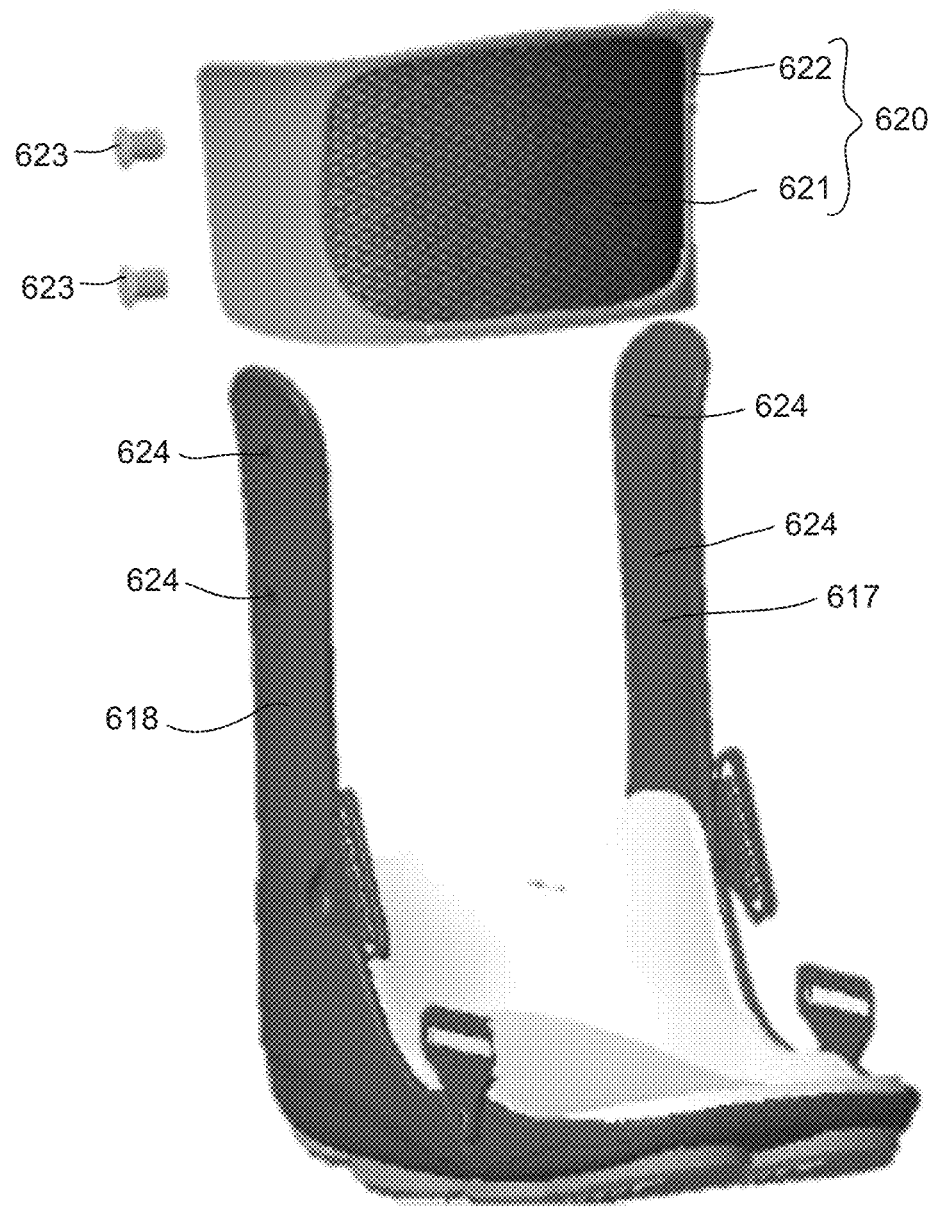
FIG. 20 illustrates a perspective, exploded view of a walker of an embodiment of the present disclosure.

In another example embodiment, referring to FIG. 20, a walker 600 may include a tibial body 620 that includes a padded plate 621 and a tibial plate frame 622. The tibial plate frame 622 may be configured to slip over stirrups (e.g. the left side body 617 and the right side body 618). According to an embodiment, the tibial plate frame 622 may include interior spaces that are configured to receive the stirrups. The walker 600 may further include fasteners 623 (e.g. projecting bodies) that are configured to be inserted through holes 624 of the left side body 617 and the right side body 618 and through the tibial plate frame 622 (and/or the padded plate 621) to fix the tibial plate frame 622 (and/or the padded plate 621) to the stirrups. In such configuration, the tibial body 620 may be rigidly fixed to the left side body 617 and the right side body 618.

The padded plate 621 may include a tibial plate that is fully encompassed by padding to form the padded plate 621. The padded plate 621 may include a tibial support structure inside. The padded plate 621 may be attached to the tibial plate frame 622, and removable from the tibial plate frame 622.

According to embodiments, a walker with a fully-removable tibial plate with an adjustable angle may be provided. For example, the angle of the tibial plate may be adjustable to accommodate each patient and to optimize pressure transfer from a tibia of a user to the tibial plate. The tibial plate may also be fully removable from a body of the walker.

Figure 21:
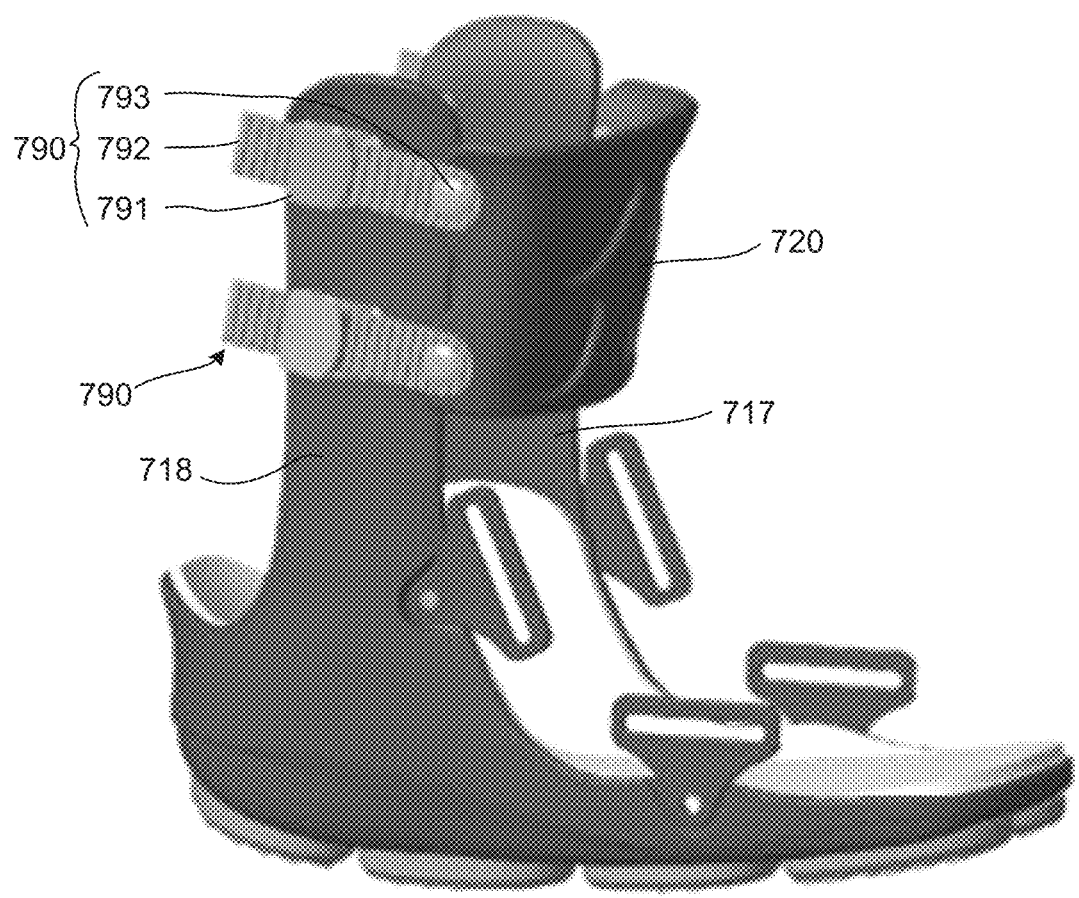
FIG. 21 illustrates a perspective view of a walker of an embodiment of the present disclosure.

In one example embodiment, referring to FIG. 21, a walker 700 may include ratchet systems 790 that are configured to attach a tibial plate 720 to a left side body 717 and a right side body 718 of the walker 700. For example, two of the ratchet systems 790 may be provided with each of the left side body 717 and the right side body 718, and one or more of the ratchet systems 790 may be adjusted to adjust an angle between a top and bottom of the tibial plate 720. According to embodiments, the ratchet systems 790 may each include a ratchet 791, a strap 792 with a plurality of stepped portions, and a fastener 793. The fastener 793 may fix a first end of the strap 792 to a part of the tibial plate 720, and the ratchet 791 may be fixed to one from among the left side body 717 and the right side body 718 and may be configured to receive the second end of the strap 792 therein. The ratchet 791 may be configured to hold one or more of the plurality of stepped portions of the strap 792 such that the strap 792 is fixed relative to the ratchet 791 in at least one direction, and may be configured to be manipulated such that the strap 792 may be freely slidable within the ratchet 791 and/or controlled by the ratchet 791 to move to a certain position. For example, the ratchet 791 may be configured to, when manipulated, pull the strap 792 further into the ratchet 791 such that the first end of the strap 792 becomes closer to the ratchet 791, thereby adjusting a position of a portion of the tibial plate 720. According to an embodiment, one or more of the ratchet systems 790 may be adjusted to adjust an angle of the tibial plate 720. According to an embodiment, the ratchet systems 790 may enable the tibial plate 720 to be fully removed and re-attached. According to one or more embodiments, each of the strap 792 of the ratchet systems 790 may be flexible and, through the configurations of the ratchet systems 790, the tibial plate 720 may be non-rigidly fixed to the left side body 717 and the right side body 718.

Figure 22:
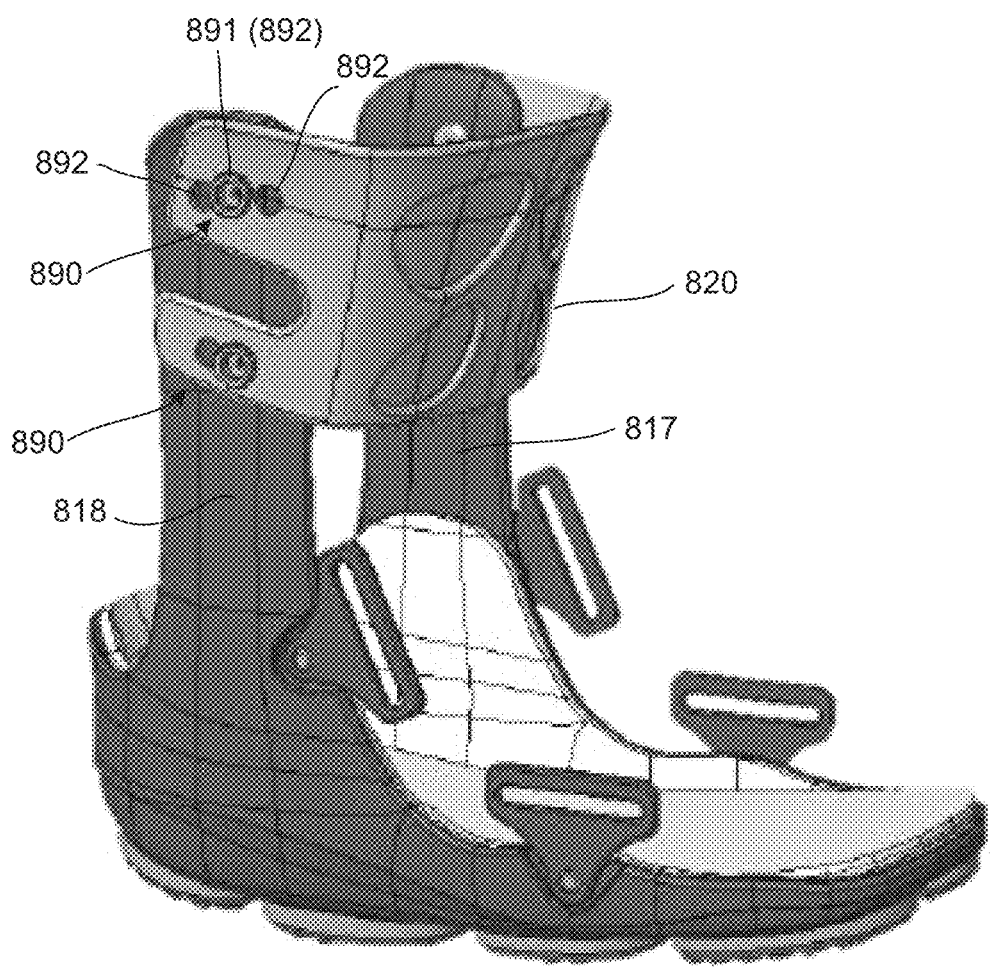
FIG. 22 illustrates a perspective view of a walker of an embodiment of the present disclosure.

In another example embodiment, referring to FIG. 22, a walker 800 may include knob systems 890 that are configured to fix a tibial body 820 (e.g. a tibial plate) to a left side body 817 and a right side body 818 of the walker 800. For example, two of the knob systems 890 may be provided with each of the left side body 817 and the right side body 818, and one or more of the knob systems 890 may be adjusted to adjust an angle of the tibial body 820 to set options. According to embodiments, the knob systems 890 may each include a knob 891 and a plurality of holes 892, within the tibial body 820. The plurality of holes 892 may communicate with each other at sides of the plurality of the holes 892. The knob 891 may be attached to one from among the left side body 817 and the right side body 818, and may be withdrawn from the left side body 817 or the right side body 818, fully or partially, such that a portion of the tibial body 820 that includes the holes 892 may be moved relative to the knob 891. For example, the portion of the tibial body 820 may be moved such that a position of the knob 891 changes from within one of the holes 892 to within another of the holes 892. Following, the knob 891 may be automatically or manually advanced into the one from among the left side body 817 and the right side body 818 such that the knob 891 fixes a position of the portion of the tibial body 820 relative to the knob 891, while the knob 891 is positioned in one of the holes 892. In other words, after the knob 891 is advanced into the one from among the left side body 817 and the right side body 818, the knob 891 may not be able to move between the holes 892 and the portion of the tibial body 820 may be set to a particular position corresponding to the one of the holes 892 in which the knob 891 is positioned. According to an embodiment, one or more of the knob systems 890 may be adjusted to adjust an angle of the tibial body 820 to set options that correspond to the holes 892. While each knob 891 of the knob systems 890 is an a closed position (an advanced position), the tibial body 820 may be rigidly fixed to the left side body 817 and the right side body 818.

According to embodiments, a walker with a partially-fixed tibial plate with an adjustable angle may be provided. For example, the tibial plate may be configured to be at least partially rigidly fixed with respect to a body of the walker to allow for angle adjustment, but not fully removable from the body of the walker.

Figure 23:
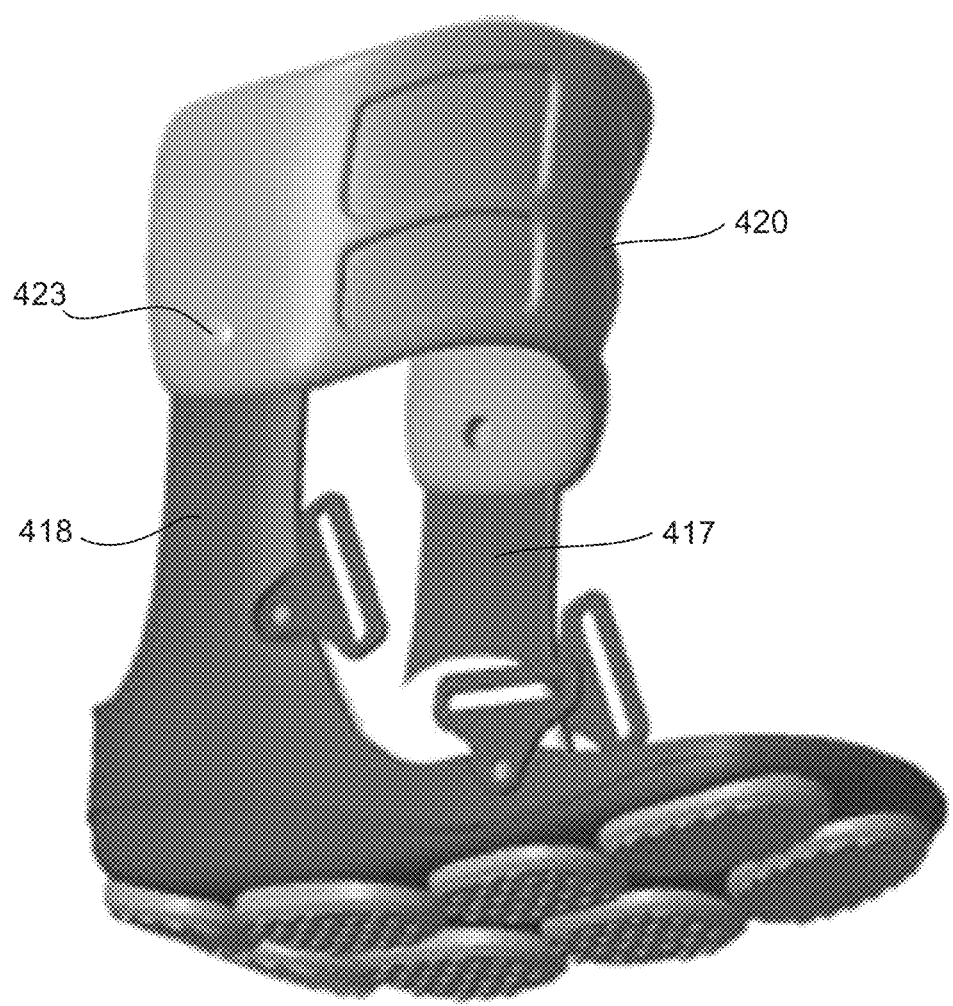
FIG. 23 illustrates a perspective view of a walker of an embodiment of the present disclosure.

In one example embodiment, referring to FIG. 23, a walker 900 may be provided. The walker 900 may be similar to the walker 400, illustrated in FIG. 18, except includes at least the following differences. The walker 900 may only include fasteners 423 (e.g. rivets) at specified points (e.g. a bottom side) of the tibial body 420. Accordingly, the tibial body 420 may rotate around an axis that extends through the fasteners 423 such that an angle of the tibial body 420 may be changed. Also, by using the fasteners 423, at least a portion of the tibial body 420 may be rigidly fixed to the left side body 417 and the right side body 418.

According to an embodiment, the walker 900 may further include one or more adjusting systems to adjust a position of a side (e.g. a top side) of the tibial body 420 that is not fixed with fasteners 423. For example, the adjusting system may include hook-and-loop straps that are attached to one or more parts of the tibial body 420. The hook-and-loop straps may be, for example, wrapped around a leg of a user of the walker 900 and fastened such that a tension of the straps urges the part of the tibial body 420 to a particular position to control an angle of the tibial body 420. The straps may also be adjusted to change the angle of the tibial body 420.

Figure 24:
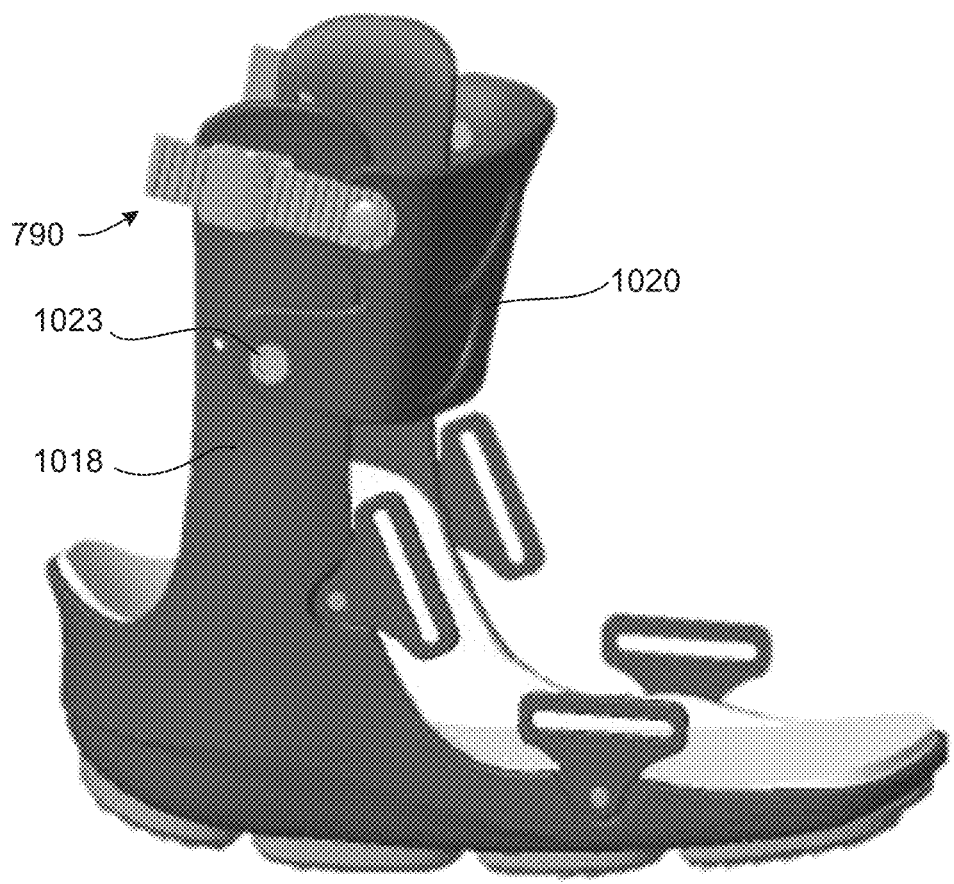
FIG. 24 illustrates a perspective view of a walker of an embodiment of the present disclosure.

According to another example embodiment, with reference to FIG. 24, a walker 1000 may be provided. The walker 1000 may include a left side body and a right side body 1018, a tibial body 1020 (e.g. a tibial plate), fasteners 1023, and ratchet systems 790 (refer to FIG. 21). In a similar manner to the fasteners 423, discussed above with respect to the walker 900 illustrated in FIG. 23, the fasteners 1023 may be provided at specified points (e.g. a bottom side) of the tibial body 1020 such that the tibial body 1020 may rotate around an axis that extends through the fasteners 1023, so that an angle of the tibial body 1020 may be changed while the tibial body 1020 is still rigidly fixed by the fasteners 1023. Also, similar to the walker 900, the walker 1000 may include one or more adjusting systems. As shown in FIG. 24, the adjusting systems may be a pair of the ratchet systems 790 that may adjust a position of the top of the tibial body 1020 so as to adjust an angle of the tibial body 1020.

Figure 25:
FIG. 25 illustrates a perspective view of a walker of an embodiment of the present disclosure.

According to another example embodiment, with reference to FIG. 25, a walker 1200 may be provided. The walker 1200 may be similar to the walker 1000 and the walker 1100, illustrated in FIGS. 18 and 19, respectively, except includes a different adjusting system. That is, the walker 1200 includes a cord system 1190 as the adjusting system. The cord system may include fixing portions 1191, cords 1192, and an adjustment body 1193. The fixing portions 1191 may be fixed on a left side body, a right side body 1018, and tibial body 1020 of the walker 1200, and the fixing portions 1191 may be configured to fix or guide a position of the cords 1192. The adjustment body 1193 may be provided (e.g. fixed) on a front of the tibial body 1020, and may be configured to adjust a tension in the cords 1192 so as to adjust a position of top of the tibial body 1020 such that an angle of the tibial body 1020 is adjusted. For example, the adjustment body 1193 may be configured to be manipulated (e.g. rotated) to adjust the tension in the cords 1192, such as by being a Boa® fit system with an adjustable dial and laces.

According to embodiments, a walker with a non-rigidly fixed tibial plate with an adjustable angle may be provided. For example, the tibial plate be configured to be non-rigidly fixed with respect to a body of the walker while still allowing for angle adjustment.

Figure 26:
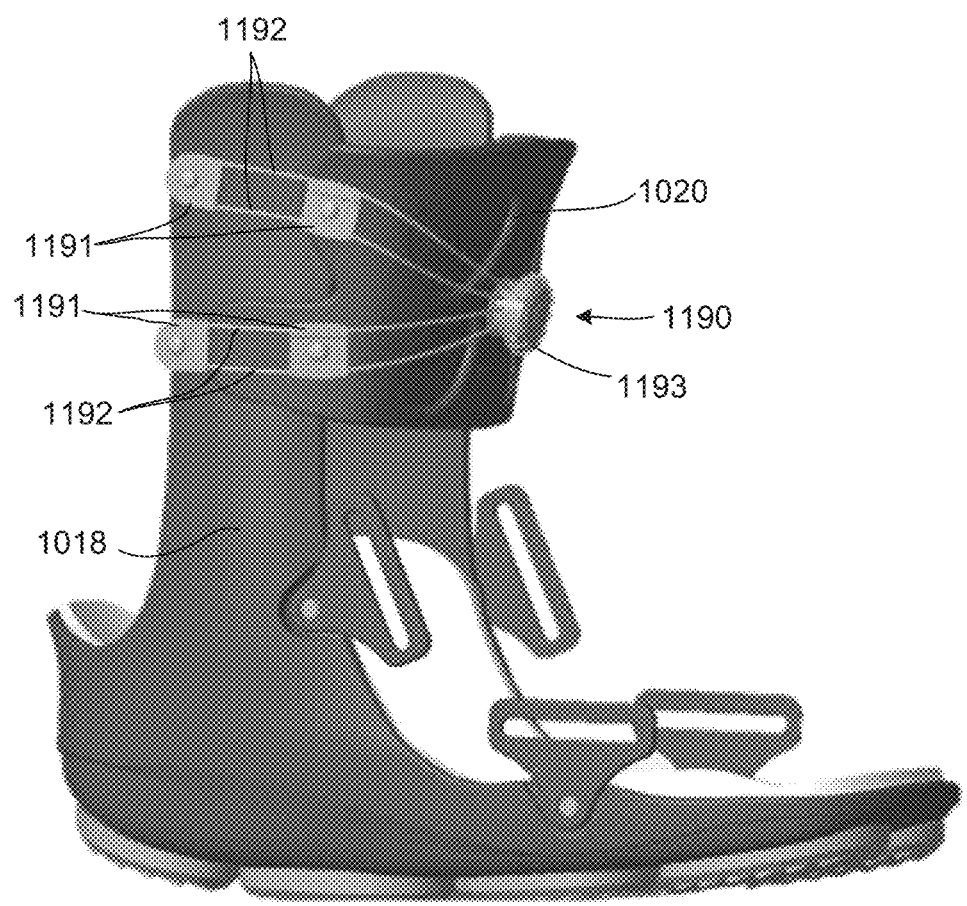
FIG. 26 illustrates a perspective view of a walker of an embodiment of the present disclosure.

In one example embodiment, referring to FIG. 26, a walker 1200 may be provided. The walker 1200 may be similar to the walker 1100, illustrated in FIG. 25, except the fasteners 1023 may be replaced with an additional portion of the cord system 1190. For example, the cord system 1190 may include an additional set of fixing portions 1191 and cords 1192 at the bottom side of the tibial body 1020 that are attached to both the left side body and the right side body 1018 of the walker 1200.

Embodiments of the present disclosure provide walkers and walker shells that may be more lightweight and have stronger structures, while enabling a reduction in plantar pressure by limiting ankle joint movement and providing pressure offloading. Moreover, embodiments of the present disclosure provide walkers and walker shells that are capable of being applied to users having a large range of calf sizes. Thus, embodiments of the present disclosure may provide an advantageous treatment option in cases related to, for example, forefoot surgery, forefoot trauma, and diabetes-related foot issues.

The term "or" as used herein is an inclusive "or", and has a meaning equivalent to "and/or."

Embodiments of the present disclosure may achieve the advantages described herein. It should also be appreciated that various modifications, adaptations, and alternative embodiments thereof may be made within the scope and spirit of the present disclosure.

What is claimed is:

1. A shell for a walker, the shell comprising:
 a base configured to receive a foot of a user thereon;
 a pair of side bodies extending upwards from the base and that are rigid, the pair of side bodies configured to cover a left side and a right side of at least one from among an ankle and a part of a lower leg of the user, respectively, while the foot of the user is received by the base; and
 a tibial body that is rigid and fixed to each of the pair of side bodies, the tibial body configured to cover a tibia of the user, without also covering a top side of the foot, while the foot of the user is received by the base,
 wherein the tibial body and the pair of side bodies are rigid such that the shell is configured to prevent ankle joint movement of the user,
 in a top view of the shell, the tibial body has a triangular shape that is configured to offload pressure applied to the tibia of the user by avoiding contact with the tibia while causing a gastrocnemius muscle and a tibialis anterior muscle of the user to absorb forces applied by the tibial body,
 the tibial body is integrally formed with each of the pair of side bodies,
 a bottom end of the tibial body extends integrally from top ends of the pair of side bodies, and
 an inner surface of the tibial body extends laterally and medially to an interior vertex portion of the tibial body such that the inner surface of the tibial body has an angle that is configured to prevent the tibial body from contacting with the tibia.

2. The shell of claim 1, wherein the pair of side bodies are integrally formed with the base.

3. The walker of claim 2, further comprising a tibial liner, wherein at least one from among the tibial body and the pair of side bodies is configured to connect to the tibial liner.

4. The shell of claim 1, wherein the shell is configured to receive the foot of the user at a rear side of the shell via an opening provided between rear sides of the pair of side bodies.

5. The shell of claim 4, wherein the pair of side bodies or the tibial body is configured to connect to a strap that extends across a calf of the user by extending across the opening.

6. The shell of claim 1, wherein at least one from among the tibial body and the pair of side bodies is configured to connect to a tibial liner.

7. The shell of claim 1, wherein at least a portion of the tibial body is rigidly fixed to each of the pair of side bodies.

8. The shell of claim 1, wherein at least one from among the base and the pair of side bodies is configured to connect to a strap that extends across the top side of the foot of the user or a front side of the ankle of the user.

9. The shell of claim 1, wherein the pair of side bodies are inclined from the base towards a front side of the shell such that the top ends of the pair of side bodies are fixed to the bottom end of the tibial body at the front side of the shell.

10. The shell of claim 1, wherein the tibial body and the pair of side bodies are formed of at least one from among nylon, polypropylene, polycarbonate (PC), acrylonitrile butadiene styrene (ABS), aluminum, and steel.

11. A walker comprising:
 a liner of the walker configured to surround a portion of a foot of a user and a part of a lower leg of the user; and
 a shell of the walker comprising:
  a base configured to receive the foot of the user, within the liner, there on;
  a pair of side bodies extending upwards from the base and that are rigid, the pair of side bodies configured to cover a left side and a right side of at least one from among an ankle and the part of the lower leg of the user, respectively, while the foot of the user is received by the base; and
  a tibial body that is rigid and fixed to each of the pair of side bodies, the tibial body configured to cover a tibia of the user, without also covering a top side of the foot, while the foot of the user is received by the base,
 wherein the tibial body and the pair of side bodies are rigid such that the shell is configured to prevent ankle joint movement of the user,
 in a top view of the shell, the tibial body has a triangular shape that is configured to offload pressure applied to the tibia of the user by avoiding contact with the tibia while causing a gastrocnemius muscle and a tibialis anterior muscle of the user to absorb forces applied by the tibial body,
 the tibial body is integrally formed with each of the pair of side bodies,
 a bottom end of the tibial body extends integrally from top ends of the pair of side bodies and
 an inner surface of the tibial body extends laterally and medially to an interior vertex portion of the tibial body such that the inner surface of the tibial body has an ankle that is configured to prevent the tibial body from contacting with the tibia.

12. The walker of claim 11, wherein the shell is configured to receive the foot of the user at a rear side of the shell via an opening provided between rear sides of the pair of side bodies.

13. The walker of claim 12, further comprising a strap, wherein the pair of side bodies or the tibial body is configured to connect to the strap such that the strap extends across a calf of the user by extending across the opening.

14. The walker of claim 11, wherein the pair of side bodies are integrally formed with the base.

15. The walker of claim 11, further comprising a strap, wherein at least one from among the base and the pair of side bodies is configured to connect to the strap such that the strap extends across the top side of the foot of the user or a front side of the ankle of the user.

16. A rear-entry walker comprising:

a shell of the rear-entry walker, the shell comprising:
- a base configured to receive a foot of a user thereon;
- a pair of side bodies extending upwards from the base and that are rigid, the pair of side bodies configured to cover a left side and a right side of at least one from among an ankle and a part of a lower leg of the user, respectively, while the foot of the user is received by the base; and
- a tibial body that is rigid and fixed to each of the pair of side bodies, the tibial body configured to cover a tibia of the user, without also covering a top side of the foot, while the foot of the user is received by the base, wherein the shell is configured to receive the foot of the user at a rear side of the shell via an opening provided between rear sides of the pair of side bodies, the tibial body and the pair of side bodies are rigid such that the shell is configured to prevent ankle joint movement of the user, in a top view of the shell, the tibial body has a triangular shape that is configured to offload pressure applied to the tibia of the user by avoiding contact with the tibia while causing a gastrocnemius muscle and a tibialis anterior muscle of the user to absorb forces applied by the tibial body, the tibial body is integrally formed with each of the pair of side bodies, a bottom end of the tibial body extends integrally from top ends of the pair of side bodies and an inner surface of the tibial body extends laterally and medially to an interior vertex portion of the tibial body such that the inner surface of the tibial body has an ankle that is configured to prevent the tibial body from contacting with the tibia.

17. The rear-entry walker of claim 16, further comprising:

a tibial liner provided on the inner surface of the tibial body.

18. The rear-entry walker of claim 17, wherein at least one from among the tibial body and the pair of side bodies is connected to the tibial liner.

* * * * *